(12) United States Patent
Nebuya

(10) Patent No.: US 12,405,324 B2
(45) Date of Patent: Sep. 2, 2025

(54) MEASUREMENT APPARATUS AND MEASUREMENT METHOD

(71) Applicant: ASAHI INTECC CO., LTD., Seto (JP)

(72) Inventor: Satoru Nebuya, Tokyo (JP)

(73) Assignee: ASAHI INTECC CO., LTD., Seto (JP)

( * ) Notice: Subject to any disclaimer, the term of this patent is extended or adjusted under 35 U.S.C. 154(b) by 283 days.

(21) Appl. No.: 18/143,939

(22) Filed: May 5, 2023

(65) Prior Publication Data

US 2023/0305084 A1  Sep. 28, 2023

Related U.S. Application Data

(63) Continuation of application No. PCT/JP2020/042112, filed on Nov. 11, 2020.

(51) Int. Cl.
*G01R 33/24* (2006.01)
*A61B 5/0536* (2021.01)
*A61B 5/055* (2006.01)
*G01R 33/44* (2006.01)
*G01R 33/54* (2006.01)

(52) U.S. Cl.
CPC ............ *G01R 33/24* (2013.01); *A61B 5/0536* (2013.01); *A61B 5/055* (2013.01); *G01R 33/443* (2013.01); *G01R 33/543* (2013.01)

(58) Field of Classification Search
None
See application file for complete search history.

(56) References Cited

U.S. PATENT DOCUMENTS

| | | | | |
|---|---|---|---|---|
| 3,932,805 A | * | 1/1976 | Abe | G01R 33/3808 324/309 |
| 5,421,345 A | * | 6/1995 | Lekholm | A61B 5/0535 600/506 |
| 6,397,095 B1 | * | 5/2002 | Eyuboglu | G01R 33/54 324/309 |
| 2014/0031901 A1 | * | 1/2014 | Zhu | A61N 1/36128 607/60 |
| 2014/0239951 A1 | * | 8/2014 | Van Lier | A61B 5/055 324/309 |

(Continued)

FOREIGN PATENT DOCUMENTS

| | | |
|---|---|---|
| JP | H06-225860 A | 8/1994 |
| JP | 2006-502809 A | 1/2006 |

(Continued)

*Primary Examiner* — Rodney E Fuller
(74) *Attorney, Agent, or Firm* — Oliff PLC

(57) ABSTRACT

A measurement apparatus including: a static magnetic field applying part that applies a static magnetic field having a constant magnitude in a first direction to a measurement target; a plurality of current applying parts applying a plurality of AC currents oriented in a plurality of directions toward a portion of the measurement target via an electrode pair; a magnetic field detecting element that detects a magnitude of a magnetic field generated from the portion of the measurement target in response to the static magnetic field having the constant magnitude in the first direction and the plurality of AC currents; a calculating part for calculating impedance of the portion of the measurement target; and an internal information output part for generating information including an internal component of the measurement target.

19 Claims, 12 Drawing Sheets

(56) References Cited

U.S. PATENT DOCUMENTS

2017/0071499 A1* 3/2017 Nebuya ................ A61B 5/0536
2020/0359898 A1* 11/2020 Gleich ................ A61B 5/0035

FOREIGN PATENT DOCUMENTS

| JP | 2009-119204 A | 6/2009 |
| JP | 5839527 B1 | 1/2016 |
| JP | 6506466 B1 | 4/2019 |
| JP | 2020-531150 A | 11/2020 |
| WO | 2015-129756 A1 | 9/2015 |
| WO | 2019/038083 A1 | 2/2019 |

* cited by examiner

MEASUREMENT APPARATUS AND MEASUREMENT METHOD

CROSS-REFERENCE TO RELATED APPLICATIONS

The present application is a bypass continuation application of International Application number PCT/JP2020/042112, filed on Nov. 11, 2020. The contents of the prior application are incorporated herein by reference in their entirety.

BACKGROUND OF THE INVENTION

The present disclosure relates to a measurement apparatus and a measurement method for measuring information inside a measurement target. A magnetic resonance imaging (MRI) method of outputting information about the inside of a living body as a tomographic image by using a nuclear magnetic resonance phenomenon is known. Also, small and highly sensitive magnetic sensors are known (see Japanese Patent No. 6506466 and Japanese Patent No. 5839527, for example).

With MRI, a static magnetic field is applied from the outside to a living body that is a measurement target, and the living body is macroscopically magnetized. Due to this, since atoms constituting a living body experience precession, when a pulse of an electromagnetic wave having a frequency corresponding to the Larmor frequency of this precession is radiated, resonance occurs, and the rotation speed of the precession changes (nuclear magnetic resonance phenomenon). When the pulse radiation of the electromagnetic wave is stopped, the precession of the atoms returns to a steady state. Since the process (relaxation phenomenon) until returning to such a steady state varies depending on the atoms, MRI generates such a difference in the relaxation phenomenon as an image, and outputs this image as a tomographic image of a living body.

As described above, since MRI includes observing the relaxation phenomenon until the precession of the atoms returns to the steady state, the measurement result cannot be output unless at least a relaxation time has elapsed. On the other hand, in order to detect an abnormality in a living body, it is desirable to acquire and determine a plurality of tomographic images at different positions in the living body, and even if a part of the living body is determined to be normal or abnormal, a measurement time from tens of minutes to one hour or more might be taken.

BRIEF SUMMARY OF THE INVENTION

The present disclosure has been made in view of the above circumstances, and it is an object of the present disclosure to obtain information about the inside of a living body at high speed with a simple configuration.

According to a first aspect of the present disclosure, provided is a measurement apparatus including: a static magnetic field applying part that applies a static magnetic field having a constant magnitude in a first direction to a measurement target; a plurality of current applying parts that apply a plurality of AC currents oriented in a plurality of directions toward a portion of the measurement target, via a pair of electrodes; a magnetic field detecting element that detects a magnitude of a magnetic field of an electromagnetic wave generated due to nuclear magnetic resonance in the portion of the measurement target generated in response to (i) the static magnetic field having the constant magnitude in the first direction and (ii) the plurality of AC currents; a calculating part that calculates impedance of the portion of the measurement target based on a detection result of the magnetic field detecting element; and an internal information output part that generates information including an internal component of the measurement target, based on the calculated impedance.

A second aspect of the present disclosure is a measurement apparatus including: in a state in which a measurement target is magnetized by geomagnetism, a plurality of current applying parts that apply a plurality of AC currents oriented in a plurality of directions, which are different from a direction of a magnetic field of the geomagnetism, toward a portion of the measurement target via a pair of electrodes; a magnetic field detecting element that detects a magnitude of a magnetic field of an electromagnetic wave generated due to nuclear magnetic resonance in the portion of the measurement target generated in response to (i) a static magnetic field caused by the geomagnetism and (ii) the plurality of AC currents; a calculating part that calculates impedance of the portion of the measurement target based on a detection result of the magnetic field detecting element; and an internal information output part that generates information including an internal component of the measurement target, based on the calculated impedance.

A third aspect of the present disclosure is a measurement method including: applying a plurality of AC currents oriented in a plurality of directions toward a portion of the measurement target, through a pair of electrodes; detecting a magnitude of a magnetic field generated from the portion of the measurement target in response to the plurality of AC currents; calculating impedance of the portion of the measurement target based on a detection result of the magnetic field; and generating and outputting information indicating an internal component of the measurement target, based on the calculated impedance.

DETAILED DESCRIPTION OF THE INVENTION

Hereinafter, the present disclosure will be described through exemplary embodiments, but the following exemplary embodiments do not limit the scope of the claims, and not all of the combinations of features described in the exemplary embodiments are necessarily essential to the solution means of the disclosure.

<First Configuration Example of a Measurement Apparatus 100>

Figure 1:
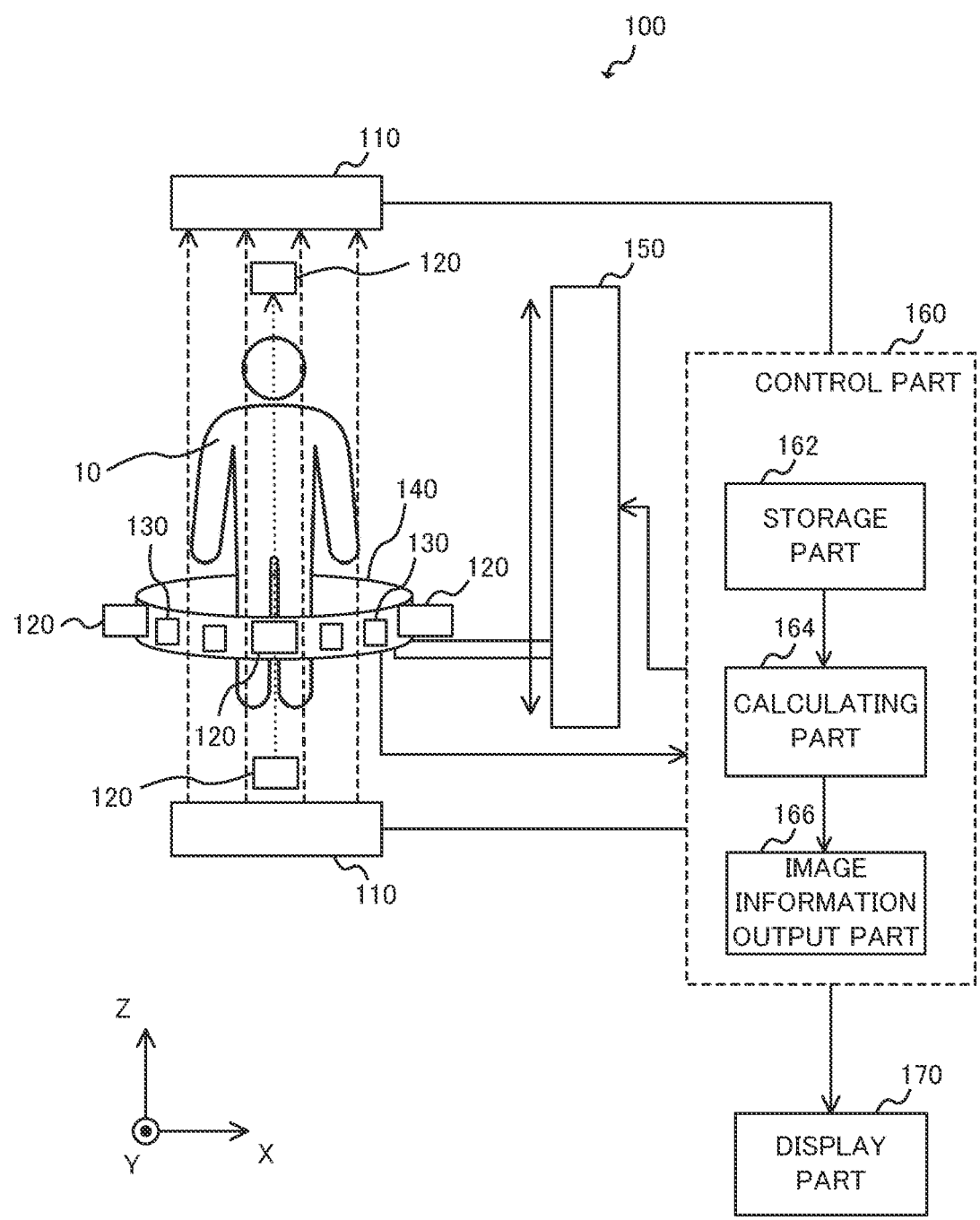
FIG. 1 shows a first configuration example of a measurement apparatus 100 according to the present embodiment, together with a measurement target 10.

FIG. 1 shows a first configuration example of a measurement apparatus 100 according to the present embodiment, together with a measurement target 10. The measurement apparatus 100 of the first configuration example outputs information about the inside of the measurement target 10 as a tomographic image. The measurement apparatus 100 applies a deflection magnetic field to a measurement target 10 to which a static magnetic field is applied, and acquires information about the inside of the measurement target 10 based on electromagnetic waves generated in response to the application of the deflection magnetic field. The measurement target 10 is, for example, a living body such as a human body. In the present embodiment, an example in which the measurement target 10 is a human body will be described. The measurement apparatus 100 includes a static magnetic field applying part 110, a deflection magnetic field applying part 120, a magnetic field detecting element 130, a mounting part 140, a moving part 150, a control part 160, and a display part 170.

The static magnetic field applying part 110 applies a static magnetic field having a constant magnitude in a first direction to the measurement target 10. FIG. 1 shows an example in which a human body serving as a measurement target 10 stands upright on a ground surface parallel to an XY plane. In FIG. 1, the first direction is shown as a direction substantially parallel to a Z direction. Here, the Z direction is a direction perpendicular to the ground surface, which is the height direction of the human body. The static magnetic field applying part 110 applies a static magnetic field having a magnitude of several T (tesla), for example, which is the same as the magnitude of the static magnetic field used in the MRI or the like, to the entire measurement target 10. The static magnetic field applying part 110 may apply a static magnetic field having a magnitude less than several T. For example, the static magnetic field applying part 110 applies a static magnetic field having a magnitude of 100 µT or more, which is larger than the magnitude of geomagnetism, to the measurement target 10. The static magnetic field applying part 110 includes a Helmholtz coil, for example.

The deflection magnetic field applying part 120 applies a deflection magnetic field that has a predetermined frequency and is oriented in a second direction, which is different from the first direction, to a part of the measurement target 10 via a coil. Here, the predetermined frequency is determined based on the magnitude of the static magnetic field output from the static magnetic field applying part 110, and is a frequency of about several kilohertz to hundreds of kilohertz, for example.

The second direction is determined based on a region to be observed in the measurement target 10, and is one or more directions different from the first direction. For example, the deflection magnetic field applying part 120 applies one or more deflection magnetic fields oriented in one or more directions different from the first direction toward a part of the measurement target 10.

The deflection magnetic field applying part 120 includes one or more magnetic field generating coils. The magnetic field generating coil is a Helmholtz coil, for example. It is desirable that the deflection magnetic field applying part 120 can apply a deflection magnetic field in various directions to the measurement target 10. At least six deflection magnetic field applying parts 120 are provided so as to apply the deflection magnetic field in six directions including the ±X direction, the ±Y direction, and the ±Z direction, for example.

In this case, it is desirable that the six deflection magnetic field applying parts 120 are arranged so that deflection magnetic fields of various sizes and directions can be applied to arbitrary portions of the measurement target 10 by controlling the magnitudes of the deflection magnetic fields output from the six deflection magnetic field applying parts 120. Further, each of the deflection magnetic field applying parts 120 may be movable so that the deflection magnetic field can be applied to various portions of the measurement target 10.

The magnetic field detecting element 130 is disposed around the measurement target 10, and detects the magnitude of each magnetic field based on electromagnetic waves generated and propagated in a part of the measurement target 10 caused by the application of a deflection magnetic field. It is desirable for a plurality of magnetic field detecting elements 130 to be disposed to surround the measurement target 10. The magnetic field detecting element 130 is a highly sensitive magnetic sensor capable of detecting weak magnetic fields in units of nT (nanoteslas), pT (picoteslas), and fT (femtoteslas), for example.

The mounting part 140 has at least some of the deflection magnetic field applying parts 120 mounted thereon. The mounting part 140 has a ring shape or partial ring shape surrounding the measurement target 10, for example, and has a plurality of deflection magnetic field applying parts 120 mounted thereon. The mounting part 140 has at least some of the plurality of magnetic field detecting elements 130 mounted thereon. FIG. 1 shows an example in which the mounting part 140 has some of the deflection magnetic field applying parts 120 and all the magnetic field detecting elements 130 mounted thereon.

With such a mounting part 140, the deflection magnetic field applying parts 120 can apply a plurality of deflection magnetic fields oriented in a plurality of directions, different from the first direction, from the plurality of deflection magnetic field applying parts 120 toward a part of the measurement target 10. The plurality of magnetic field detecting elements 130 can detect magnetic fields generated in a plurality of directions caused by applying a plurality of deflection magnetic fields.

The moving part 150 moves the mounting part 140 in a predetermined direction while maintaining the directions of the deflection magnetic fields generated by the plurality of deflection magnetic field applying parts 120 with respect to the measurement target 10. The moving part 150 moves the mounting part 140 in a direction parallel to or perpendicular to the measurement target 10. FIG. 1 shows an example in which the moving part 150 moves the mounting part 140 in the first direction. It is desirable that the moving part 150 can move the mounting part 140 in such a manner that deflection magnetic fields can be applied to a designated portion from the feet to the head of the human body. Further, the moving part 150 may move the mounting part 140 so as to rotate around the measurement target 10.

The mounting part 140 may have a cylindrical shape surrounding the measurement target 10. The mounting part 140 has a cylindrical shape extending in the first direction, for example. In this case, the deflection magnetic field applying parts 120 and the magnetic field detecting elements 130 may be provided at a plurality of different locations on the mounting part 140. For example, when the mounting part 140 has a size that covers the measurement target 10, it is desirable that a plurality of deflection magnetic field applying parts 120 are arranged to apply deflection magnetic fields to a designated portion from the feet to the head of the human body. For example, the cylindrical mounting part 140 has a ring shape or a shape having a plurality of ring shapes, surrounding the measurement target 10. In this case, since the deflection magnetic field can be applied to an arbitrary portion of the measurement target 10 without moving the mounting part 140, the moving part 150 need not be provided.

The control part 160 controls operations of the static magnetic field applying part 110, the deflection magnetic field applying part 120, the magnetic field detecting element 130, the mounting part 140, and the moving part 150. The control part 160 controls the application timing of the static magnetic field by the static magnetic field applying part 110 and the application timing of the deflection magnetic field by the deflection magnetic field applying part 120, for example. The control part 160 controls the detection timing of the magnetic field detecting element 130. The control part 160 controls the moving part 150 to move the mounting part 140. The control part 160 acquires the detection result detected by the magnetic field detecting element 130. The control part 160 generates a tomographic image of the measurement target 10 based on the obtained detection result. The control part 160 is a computer such as a server, for example.

<Configuration Example of the Mounting Part 140 and Control Part 160>

Figure 2:
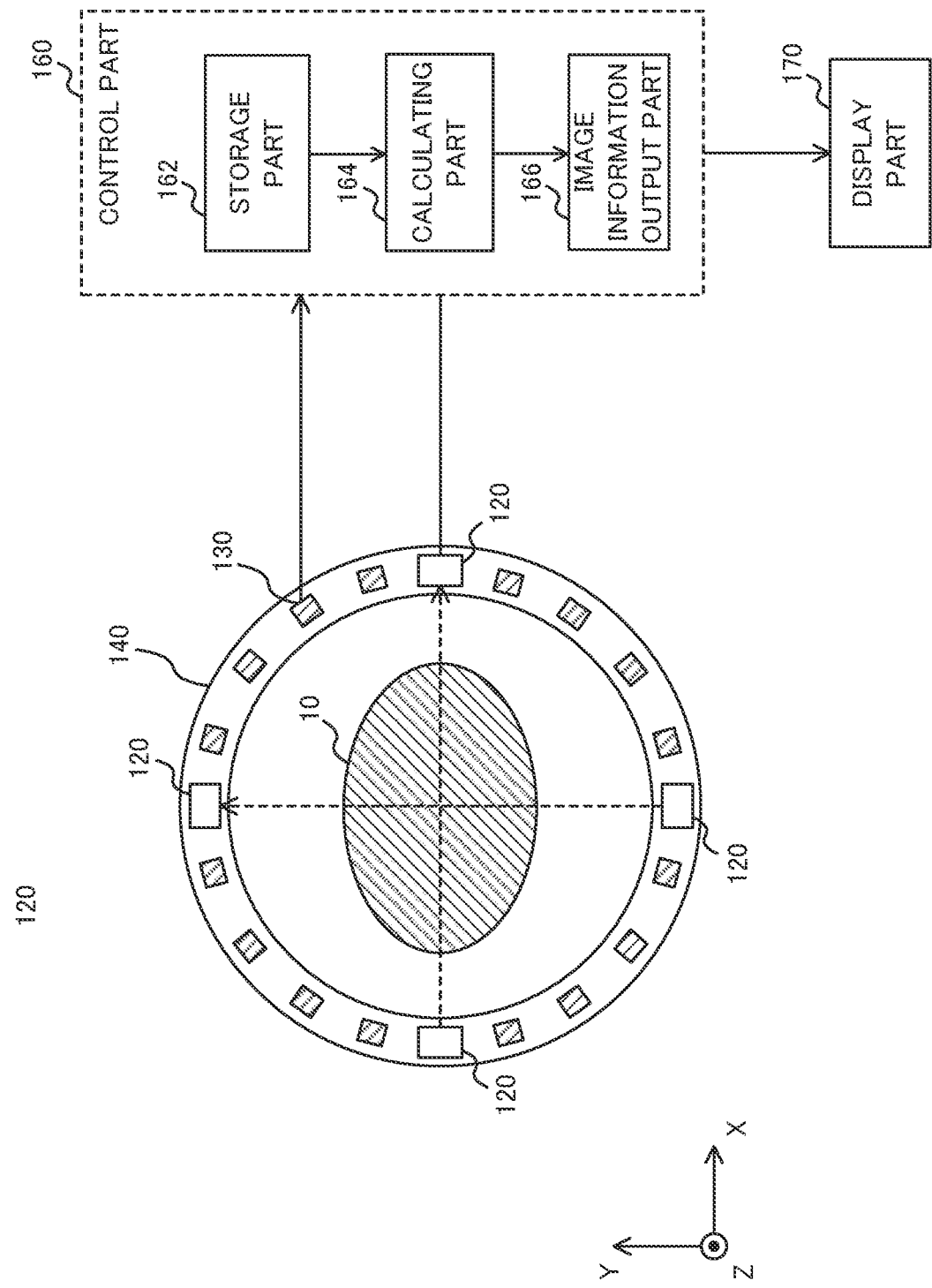
FIG. 2 shows a configuration example of a mounting part 140 and a control part 160 according to the present embodiment, together with the measurement target 10.

FIG. 2 shows a configuration example of the mounting part 140 and the control part 160 according to the present embodiment, together with the measurement target 10. FIG. 2 shows a configuration example of the mounting part 140 and the measurement target 10 in a cross section of the measurement apparatus 100 in a plane parallel to the XY plane shown in FIG. 1. As described with reference to FIG. 1, the mounting part 140 includes a plurality of deflection magnetic field applying parts 120 and a plurality of magnetic field detecting elements 130.

In the mounting part 140, the deflection magnetic field applying parts 120 and the magnetic field detecting elements 130 are provided at predetermined intervals along the circumferential direction of the ring shape, for example. The deflection magnetic field applying parts 120 are disposed so as to be able to apply a deflection magnetic field in a predetermined direction. The magnetic field detecting elements 130 are disposed so as to be able to detect the magnetic field generated from the measurement target 10.

The control part 160 applies the deflection magnetic field from the deflection magnetic field applying parts 120 to the measurement target 10 during a period in which the static magnetic field applying part 110 applies the static magnetic field to the measurement target 10. Due to this, the deflection magnetic field is applied in a state in which the measurement target 10 is macroscopically magnetized. Accordingly, in the same manner as in the MRI operation, when the frequency of the deflection magnetic field matches the Larmor frequency of the precession of the atoms forming the measurement target 10, a nuclear magnetic resonance phenomenon occurs. That is, the rotational speed of the precession of the atoms irradiated with the deflection magnetic field, among the atoms forming the measurement target 10, changes. Due to such a change in precession, an electromagnetic wave in a state different from the steady state is generated from the atoms irradiated with the deflection magnetic field.

Such nuclear magnetic resonance of the atoms is determined depending on the type of atom, the density of the atoms, the magnitude of the static magnetic field, the frequency of the deflection magnetic field, and the like. For example, if the magnitude of the static magnetic field is about 0.1 T to about 2 T, which is similar to the magnetic strength used in the MRI, nuclear magnetic resonance of hydrogen atoms in the human body can be caused by setting the frequency of the deflection magnetic field to about hundreds of kilohertz. If the magnitude of the static magnetic field is about tens of microteslas, which is similar to the magnitude of geomagnetism, nuclear magnetic resonance of hydrogen atoms in the human body can be caused by setting the frequency of the deflection magnetic field to about several kilohertz.

The magnetic field detecting element 130 detects a magnetic field component of an electromagnetic wave generated in response to such nuclear magnetic resonance. The deflection magnetic field applying part 120 applies a deflection magnetic field to a localized portion of the measurement target 10, for example. An eddy current corresponding to the deflection magnetic field is generated in a localized portion of the measurement target 10. The eddy current is a current having a magnitude corresponding to the impedance of the localized portion. Then, a magnetic field corresponding to the generated eddy current is generated. The magnetic field detecting element 130 detects the magnitude of the magnetic field generated in this manner. In this way, the magnitude of the magnetic field detected by the magnetic field detecting element 130 is a value based on the electromagnetic wave propagated under the influence of the electric characteristics of the path from the portion to which the deflection magnetic field is applied to the magnetic field detecting element 130. Here, the electrical characteristics of the path from the portion to which the deflection magnetic field is applied to the magnetic field detecting element 130 are the impedances of organs and the like in the human body, for example.

That is, the magnitude of the magnetic field detected by the magnetic field detecting element 130 corresponds to information about the inside of the human body through which the electromagnetic wave has passed. Therefore, the control part 160 controls the magnitude of the magnetic field output from the deflection magnetic field applying part 120 to apply the deflection magnetic field to a plurality of portions of the measurement target 10, and acquires the detection result of the magnetic field detecting element 130 for each portion to which the deflection magnetic field is applied. Due to this, the control part 160 can acquire the detection result of the magnetic field corresponding to the impedance distribution inside the measurement target 10. By analyzing such a detection result, the control part 160 can generate information about the inside of the measurement target 10 as an image. The control part 160 described above includes a storage part 162, a calculating part 164, and an image information output part 166, for example.

The storage part 162 stores the detection result detected by the magnetic field detecting element 130. The storage part 162 may store intermediate data, calculation results, threshold values, parameters, and the like generated (or used) during the operation of the measurement apparatus 100. The storage part 162 may supply the stored data to the request source in response to a request from each part in the measurement apparatus 100.

The storage part 162 may store an OS (Operating System) in which a server or the like functions as the control part 160, and information such as a program. The storage part 162 may store various types of information including a database referred to at the time of execution of the program. For example, a computer such as a server functions as at least a part of the storage part 162, the calculating part 164, and the image information output part 166 by executing a program stored in the storage part 162.

The storage part 162 includes a ROM (Read Only Memory) for storing a BIOS (Basic Input Output System) and the like of a computer or the like, and a RAM (Random Access Memory) serving as a work area, for example. The storage part 162 may include a large-capacity storage part such as an HDD (Hard Disk Drive) and/or an SSD (Solid State Drive). The computer may further include a GPU (Graphics Processing Unit) or the like.

Based on the detection results of the plurality of magnetic field detecting elements 130, the calculating part 164 calculates the impedance distribution of at least a portion of the region where the electromagnetic wave propagates in the measurement target 10. For example, the calculating part 164 compares and analyzes the magnitudes of the magnetic fields of the electromagnetic waves propagated from the plurality of portions, to calculate impedances between the plurality of portions. For example, the calculating part 164 calculates an impedance distribution inside the human body using a two-dimensional Fourier transform or the like.

The image information output part 166 generates and outputs an image showing information about the inside of the measurement target 10, based on the impedance distribution. The calculating part 164 and the image information output part 166 generate a tomographic image of the inside of the human body using an image reconstruction method known as computer tomography. Since the image reconstruction method is a well-known technique, a detailed description thereof is omitted here. The image information output part 166 may generate a three-dimensional image based on the two-dimensional tomographic image. The image information output part 166 displays the generated image on a display part or the like. The image information output part 166 may store the generated image in the storage part 162. Further, the image information output part 166 may store the generated image in an external database or the like, via a network or the like.

The display part 170 displays one or more images generated by the image information output part 166. As described above, the measurement apparatus 100 according to the present embodiment can output an impedance distribution of the inside of a living body such as a human body, as a tomographic image. Since the impedance of the inside of the human body varies depending on the organ or the like, the state of the inside of the human body and the like can be easily confirmed using the tomographic image output from the measurement apparatus 100.

The measurement apparatus 100 described above applies a static magnetic field and a deflection magnetic field to the measurement target 10 to generate a nuclear magnetic resonance phenomenon, and detects an electromagnetic wave based on the generation of the nuclear magnetic resonance phenomenon. Since the measurement apparatus 100 calculates the impedance distribution without observing the relaxation phenomenon occurring until the nuclear magnetic resonance phenomenon returns to the steady state, such as in MRI, it is possible to output the tomographic image of the inside of the measurement target 10 at a higher speed. In addition, a tumor such as cancer occurring in an organ or the like may change to an impedance different from the impedance of the organ. Accordingly, by using the measurement apparatus 100, the normal state, the abnormal state, and the like of the organ, which have been difficult to observe by MRI, can be easily observed and distinguished.

As described above, the measurement apparatus 100 detects the electromagnetic wave propagating in response to the nuclear magnetic resonance phenomenon generated inside the measurement target 10, thereby outputting information about the inside of the measurement target 10 as an image. Accordingly, as long as the electromagnetic wave can be detected, the magnitude of the static magnetic field applied to the measurement target 10 by the static magnetic field applying part 110 may be smaller than the magnitude of the static magnetic field up to several teslas used in MRI or the like.

In this case, the magnitude of the magnetic field to be detected by the magnetic field detecting element 130 decreases in proportion to the magnitude of the static magnetic field. However, since a magnetic sensor with high sensitivity is known as exemplified in Patent Documents 1 and 2, the magnitude of the static magnetic field output from the static magnetic field applying part 110 can be reduced from milliteslas to approximately several hundred microteslas. Due to this, the measurement apparatus 100 with a compact size can output a tomographic image of the inside of the measurement target 10 inexpensively, without using an expensive and large-sized magnetic field generating apparatus that generates strong magnetic fields of several teslas, for example.

It is also known that, as examples of a highly sensitive magnetic sensor, there are an optical pumping magnetometer, a superconducting quantum interference device SQUID, and the like that have a high sensitivity in units of approximately femtoteslas or less. In this way, when a high-sensitivity magnetic sensor capable of detecting weak magnetic fields in units of picoteslas or less is used as the magnetic field detecting element 130, the magnitude of the static magnetic field output from the static magnetic field applying part 110 can be made smaller.

For example, the static magnetic field applying part 110 may reduce the magnitude of the static magnetic field to be output to approximately the same magnitude as geomagnetism. In this case, the measurement apparatus 100 may use geomagnetism as a static magnetic field having a certain magnitude in the first direction. Then, the deflection magnetic field applying part 120 applies a deflection magnetic field in a second direction different from the first direction, which is the direction of the magnetic field of the geomagnetism, to a portion of the measurement target 10 magnetized by the geomagnetism.

In such a measurement apparatus 100, the static magnetic field applying part 110 may be omitted, and the scale of the apparatus may be further reduced. The measurement apparatus 100 may further include a fixed portion that can move the measurement target 10 while the measurement target 10 is fixed so that the first direction, which is the direction of the geomagnetism, and the predetermined direction of the measurement target 10 match each other. Further, such a fixing portion may have a bed or the like so that a human body can be fixed in a reclined state.

In the measurement apparatus 100 according to the present embodiment described above, the static magnetic field applying part 110 applies a static magnetic field with a constant magnitude to the measurement target 10, but it is not limited to this. In addition, the static magnetic field applying part 110 may be provided so that the magnitude of the static magnetic field applied to the measurement target 10 can be changed.

As described above, the resonance frequency at which nuclear magnetic resonance occurs in the measurement target 10 varies depending on the type of atoms, the magnitude of the static magnetic field, and the like. Therefore, when the static magnetic field applying part 110 changes the magnitude of the static magnetic field applied to the measurement target 10, the resonance frequency for the atoms contained in the measurement target 10 can be changed. Therefore, the control part 160 acquires the detection result from the magnetic field detecting element 130 for each magnitude of the static magnetic field output from the static magnetic field applying part 110. Due to this, the calculating part 164 calculates the impedance distribution for each magnitude of the static magnetic field.

In this way, the measurement apparatus 100 can measure the frequency characteristic of the impedance distribution by sweeping the magnitude of the static magnetic field within a predetermined range. The frequency characteristic of the impedance distribution can be expressed with the horizontal axis representing the frequency and the vertical axis representing the value of the impedance at one or more locations. Further, a tomographic image of the impedance distribution may be generated for each of a plurality of resonance frequencies to obtain the frequency characteristic of the impedance distribution. By measuring the frequency characteristic of the impedance distribution, the occurrence of nuclear magnetic resonance for a plurality of different atoms can be determined and more detailed information about the inside of the measurement target 10 can be acquired, for example.

In the measurement apparatus 100 according to the present embodiment, an example of detecting an electromagnetic wave based on the occurrence of a nuclear magnetic resonance phenomenon has been described, but the present disclosure is not limited thereto. Since the measurement apparatus 100 can generate the nuclear magnetic resonance phenomenon in the measurement target 10, a relaxation phenomenon occurring until the nuclear magnetic resonance phenomenon returns to a steady state, such as in MRI, can be observed. The following describes such a measurement apparatus 100.

<Modified Example of the Measurement Apparatus 100 of the First Configuration Example.>

Figure 3:
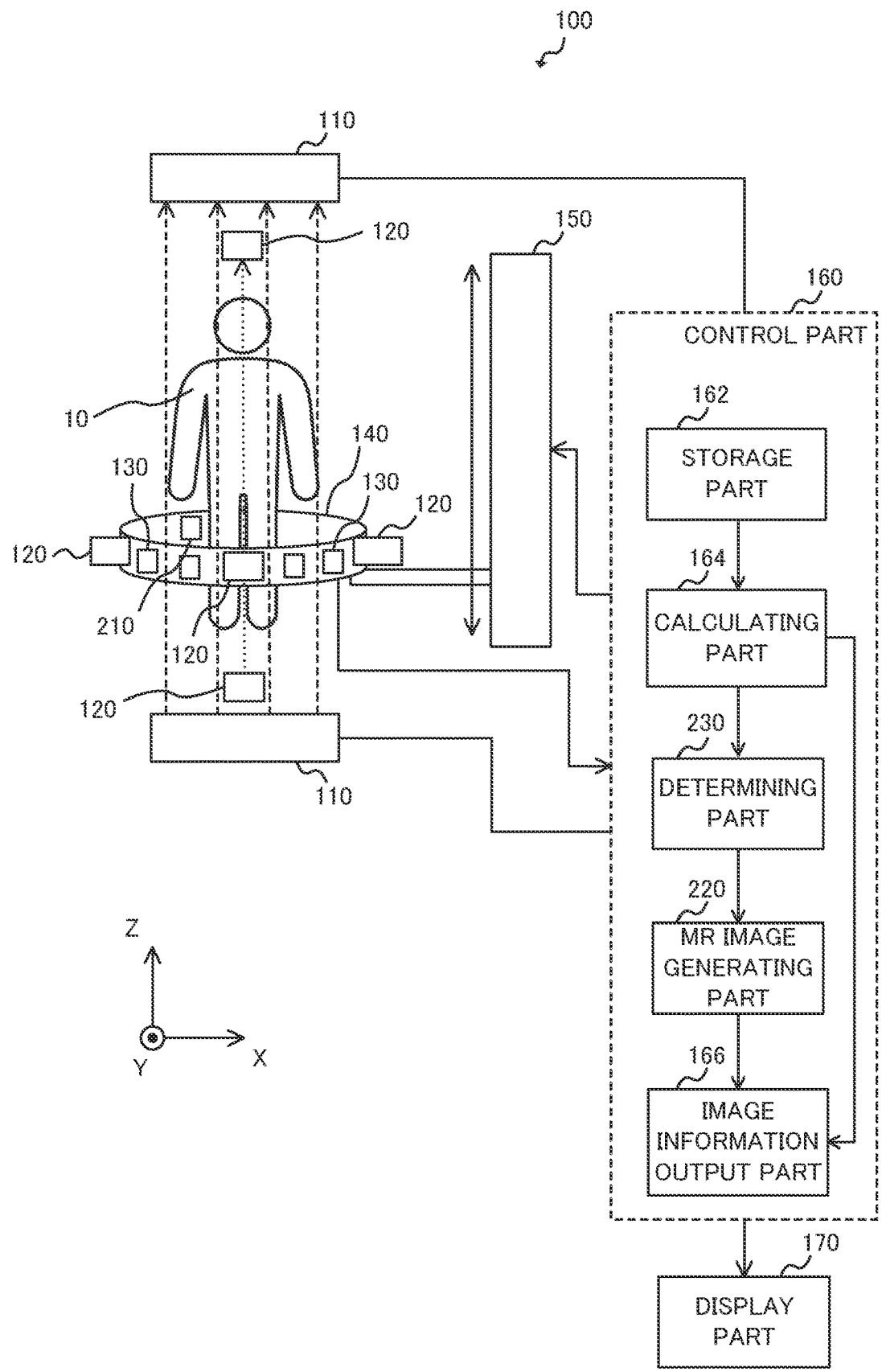
FIG. 3 shows a modified example of the measurement apparatus 100 according to the present embodiment together with the measurement target 10.

FIG. 3 shows a modified example of the measurement apparatus 100 of the first configuration example according to the present embodiment, together with the measurement target 10. In the measurement apparatus 100 of the present modification, components that are substantially the same as those of the measurement apparatus 100 according to the present embodiment shown in FIGS. 1 and 2 are denoted by the same reference numerals, and description thereof is omitted. The measurement apparatus 100 of this modification includes a relaxation detecting element 210, an MR image generating part 220, and a determining part 230.

The relaxation detecting element 210 detects a relaxation phenomenon of an electromagnetic wave generated by application of a deflection magnetic field in a portion of the measurement target 10. The relaxation detecting element 210 is a detecting element similar to the magnetic field detecting element 130, for example. Further, among the plurality of magnetic field detecting elements 130, one or more magnetic field detecting elements 130 may further function as a relaxation detecting element 210 and detect a process occurring from the detection of the magnetic field to when the magnitude of the magnetic field returns to a steady state. Since the relaxation phenomenon of an electromagnetic wave is known in MRI measurement, description thereof is omitted here. The control part 160 acquires such a relaxation phenomenon detection result from the magnetic field detecting element 130.

The MR image generating part 220 generates and outputs a magnetic resonance image, which is a tomographic image of the inside of the measurement target 10, based on the detection result of the relaxation detecting element 210. The MR image generating part 220 generates a magnetic resonance image of the inside of the human body using, for example, an image reconstruction method known as computer tomography. Since the image reconstruction method is a well-known technique, a detailed description thereof is omitted here. Due to the above, the measurement apparatus 100 can output a magnetic resonance image by reducing the scale of the measurement apparatus 100 to be smaller than that of a conventional MRI, without generating a strong magnetic field of several teslas.

In this way, the measurement apparatus 100 is configured to be able to measure a tomographic image of the impedance distribution of the measurement target 10 and a magnetic resonance image. In this case, it is desirable that the measurement apparatus 100 is configured to be capable of performing measurement by switching the tomographic image and the magnetic resonance image of the impedance distribution of the measurement target 10. Further, it is more preferable that the measurement location of the magnetic resonance image can be specified based on the measurement result of the tomographic image of the impedance distribution. In this case, the control part 160 includes a determining part 230.

The determining part 230 determines a location inside of the measurement target 10 at which to acquire the magnetic resonance image, based on one or more images indicating information about the inside of the measurement target 10 generated by the image information output part 166. Since the tomographic image of the impedance distribution of the measurement target 10 can be measured at high speed as described above, the tomographic image can be used to determine a measurement location for the magnetic resonance image, for example. In this case, the determining part 230 may use the measurement results of a plurality of tomographic images to determine the location in the measurement target 10 at which the magnetic resonance image is to be acquired.

The determining part 230 determines a location where an abnormality is estimated to be in the tomographic image as a measurement location of the magnetic resonance image, based on image processing such as image comparison, for example. Alternatively, after the image information output part 166 displays the measurement results of the plurality of tomographic images on the display part 170, the determining part 230 may receive an input of a location to be measured in the magnetic resonance image from a user or the like. The following describes such an operation of the measurement apparatus 100.

<First Example of the Operation Flow of the Measurement Apparatus 100>

Figure 4:
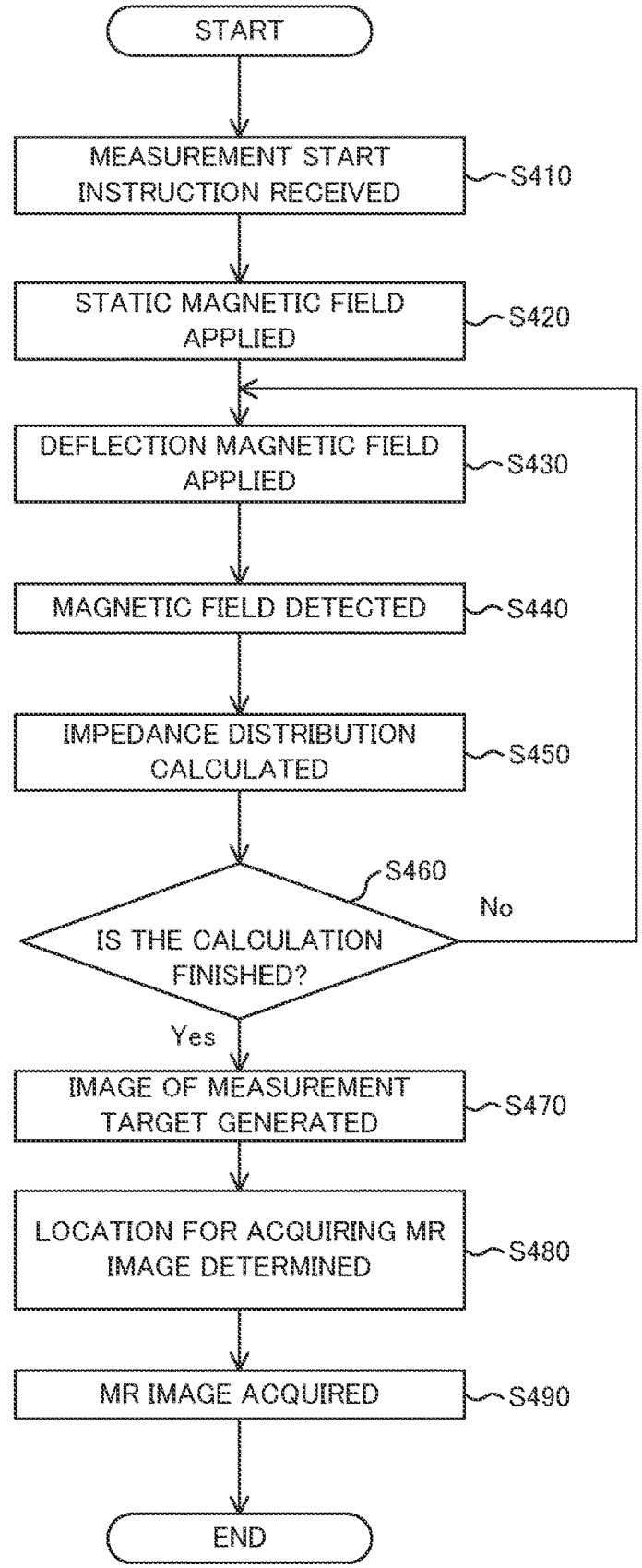
FIG. 4 shows an example of an operation flow of the measurement apparatus 100 of the present modification shown in FIG. 3.

FIG. 4 shows an example of an operation flow of the measurement apparatus 100 of the present modification shown in FIG. 3. The measurement apparatus 100 outputs a magnetic resonance image of the measurement target 10 by executing the operation flow from S410 to S490.

First, the control part 160 receives a measurement start instruction for the measurement target 10 from a user or the like (S410). Here, it is assumed that the measurement target 10 is disposed so as to have a predetermined positional relationship with respect to the static magnetic field applying part 110, the deflection magnetic field applying part 120, and the magnetic field detecting element 130. The control part 160 further receives information concerning the measurement range for the measurement target 10. For example, the control part 160 receives an instruction of a measurement range such as a head, a neck, a chest, an abdomen, a waist, a leg, the whole body, or the like. In accordance with the received information, the control part 160 controls the moving part 150 to move the mounting part 140 to a measurement start point of the measurement range.

Next, the static magnetic field applying part 110 applies a static magnetic field having a constant magnitude in the first direction to the measurement target 10 (S420). The static magnetic field applying part 110 applies a static magnetic field having a predetermined intensity level to the measurement target 10.

Next, the deflection magnetic field applying part 120 applies a deflection magnetic field that has a predetermined frequency and is oriented in a second direction, which is different from the first direction, to a portion of the measurement target 10 (S430). The deflection magnetic field applying part 120 applies a deflection magnetic field to a portion of the measurement target 10 corresponding to the received measurement range. Then, the plurality of magnetic field detecting elements 130 detect magnitudes of the magnetic fields, around the measurement target 10, based on electromagnetic waves generated and propagated in the portion of the measurement target 10 due to the application of the deflection magnetic field (S440).

Next, the calculating part 164 calculates the impedance distribution of at least a portion of the region where the electromagnetic waves propagate inside the measurement target 10, based on the detection results of the propagated electromagnetic waves (S450). The control part 160 repeats the operations of S430 to S450 until the impedance distribution of the measurement range can be calculated (S460: NO). Here, as an example, the control part 160 changes the location at which the deflection magnetic field is applied, and calculates the impedance distribution for each location at which the deflection magnetic field is applied. The control part 160 may control the moving part 150 to move the mounting part 140 in order to change the location at which the deflection magnetic field is applied.

If the impedance distribution of the measurement range can be calculated (S460: Yes), the image information output part 166 generates and outputs an image indicating information about the inside of the measurement target 10 based on the impedance distribution (S470). For example, the image information output part 166 generates one or more tomographic images corresponding to one or more impedance distributions. Alternatively or in addition to this, the image information output part 166 may generate a 3D image of the inside of the measurement target 10. For example, the image information output part 166 displays one or more generated images on the display part 170.

Next, the determining part 230 determines a location inside the measurement target 10 for a magnetic resonance image is to be acquired, based on one or more generated images indicating the information about the inside of the measurement target 10 (S480). The determining part 230 receives an input of a location where a magnetic resonance image is to be acquired from the user of the measurement apparatus 100 who has confirmed the image of the measurement target 10 displayed on the display part 170, for example.

Next, the control part 160 acquires and outputs the determined magnetic resonance image of the location in the measurement target 10 (S490). The magnetic resonance image may be acquired using a known method. For example, the static magnetic field applying part 110 applies a static magnetic field having a constant magnitude in the first direction to the measurement target 10. Then, the deflection magnetic field applying part 120 applies a deflection magnetic field that has a predetermined frequency and is oriented in a direction different from the first direction toward the determined location in the measurement target 10. The control part 160 may control the moving part 150 to move the mounting part 140 in order to apply the deflected magnetic field to the determined location in the measurement target 10.

The relaxation detecting element 210 detects an electromagnetic wave generated by the application of the deflection magnetic field and a relaxation phenomenon of the generated electromagnetic wave, at a location in the measurement target 10. The MR image generating part 220 generates and outputs a magnetic resonance image, which is a tomographic image of the inside of the measurement target, based on the detected results of the generated electromagnetic wave and the relaxation phenomenon of the electromagnetic wave. The MR image generating part 220 displays the generated magnetic resonance image on the display part 170, for example. The MR image generating part 220 may display the magnetic resonance image together with the image of the inside of the measurement target 10 displayed by the image information output part 166.

As described above, the measurement apparatus 100 according to the present modification can determine the location in the measurement target 10 at which the magnetic resonance image is to be acquired, based on the tomographic image of the impedance distribution, and can measure this magnetic resonance image. Therefore, the measurement apparatus 100 can measure and output a magnetic resonance image quickly by appropriately determining a location to be observed in the measurement target 10 with a simple configuration.

The operation flow described with reference to FIG. 4 is an example of the operation flow of the measurement apparatus 100 provided with the static magnetic field applying part 110, but the operation flow is not limited thereto. The measurement apparatus 100 may measure a tomographic image of the impedance distribution after measuring the magnetic resonance image. In a case where the measurement apparatus 100 measures an image and a magnetic resonance image of the inside of the measurement target 10 using geomagnetism, it is needless to say that the same operation can be performed by, for example, omitting the operation of S420 by the static magnetic field applying part 110 and applying a deflection magnetic field in a direction different from the first direction, which is the direction of the magnetic field of geomagnetism, to a portion of the measurement target 10.

In the measurement apparatus 100 according to the present embodiment, an example in which an image of the inside of the measurement target 10 can be quickly measured has been described. An example has been described in which the measurement apparatus 100 capable of measuring two images, namely the tomographic image and the magnetic resonance image, of the impedance distribution of the measurement target 10 can switch between executing these two measurements. Alternatively, the measurement apparatus 100 may be configured to be capable of measuring only the magnetic resonance image of the measurement target 10.

Further, in the measurement apparatus 100 according to the present embodiment described above, an example has been described in which the moving part 150 moves the mounting part 140 while the measurement target 10 is fixed, but the present disclosure is not limited thereto. For example, the mounting part 140 may be fixed, and the moving part 150 may move the measurement target 10. In this case, it is desirable that the human body serving as the measurement target 10 is fixed to a bed or the like, and the moving part 150 moves the bed.

<Configuration Example of the Detection Apparatus 400>

Figure 5:
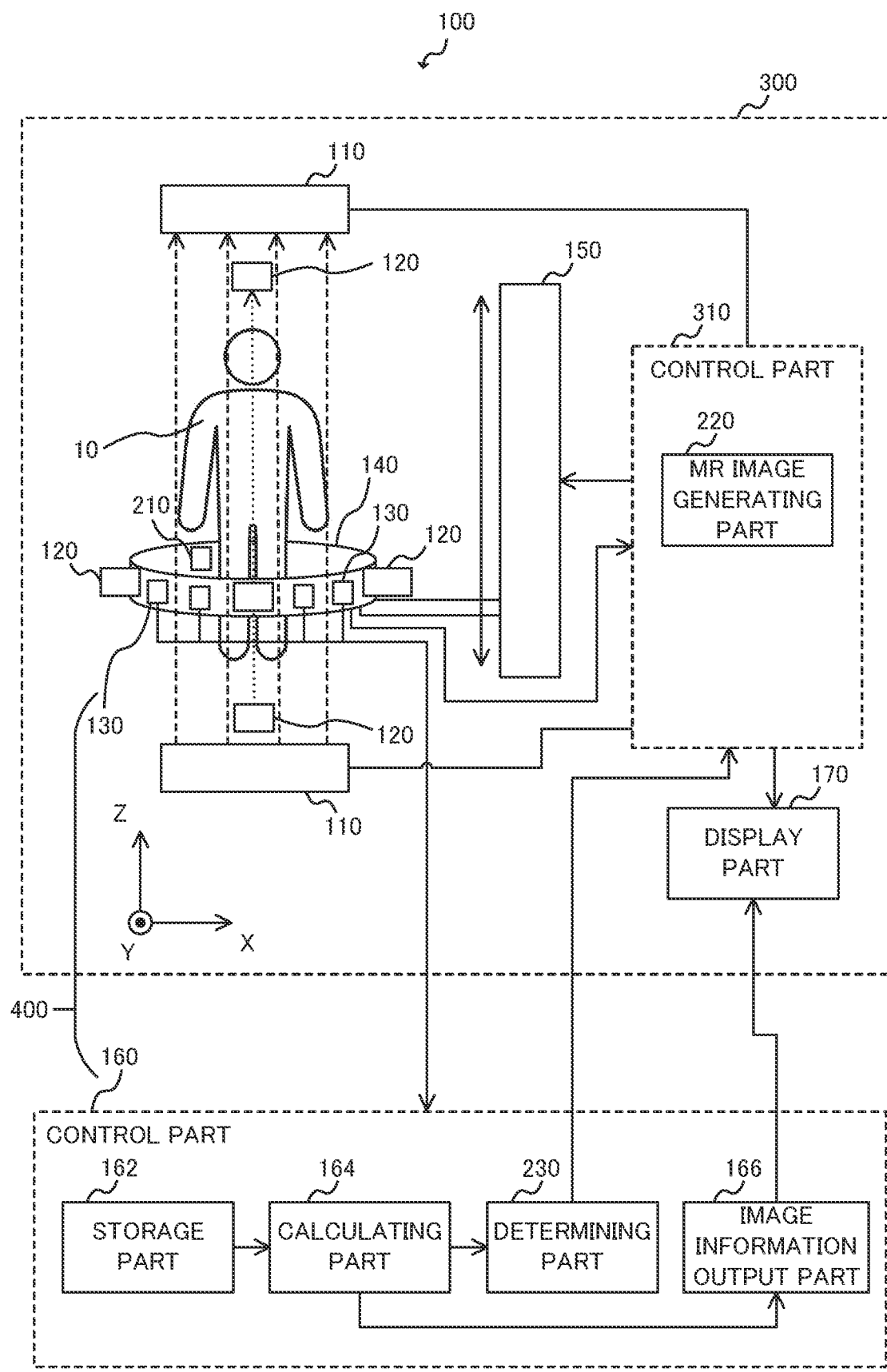
FIG. 5 shows a configuration example of a detection apparatus 400 according to the present embodiment, together with an MR image measurement apparatus 300.

Although an example in which the measurement apparatus 100 according to the present embodiment is an independent apparatus has been described, the present disclosure is not limited thereto. The measurement apparatus 100 may be an apparatus that functions by being added to an existing MR image measurement apparatus that outputs a magnetic resonance image. FIG. 5 shows a configuration example of the detection apparatus 400 according to the present embodiment, together with the MR image measurement apparatus 300.

The MR image measurement apparatus 300 includes at least a configuration that operates in the same manner as the static magnetic field applying part 110, the deflection magnetic field applying part 120, the mounting part 140, the moving part 150, the display part 170, and the relaxation detecting element 210, and the MR image generating part 220 according to the present embodiment. The MR image measurement apparatus 300 includes a control part 310 that controls each part in order to measure a magnetic resonance image. Since the measurement of the magnetic resonance image by the MR image measurement apparatus 300 is substantially the same as the operation described above, description thereof is omitted here.

The detection apparatus 400 is provided in such an MR image measurement apparatus 300. In this case, a combination of the MR image measurement apparatus 300 and the detecting apparatus 400 functions as at least a portion of the measurement apparatus 100 according to the present embodiment. The detection apparatus 400 includes a plurality of the magnetic field detecting elements 130, and the control part 160 including the storage part 162, the calculating part 164, the image information output part 166, and the determining part 230.

The detection apparatus 400 transmits and receives a control signal or the like to and from the MR image measurement apparatus 300 to generate and output an image indicating information about the inside of the measurement target 10. Further, the detection apparatus 400 may supply a control signal instructing the measurement of the magnetic resonance image to the MR image measurement apparatus 300 based on the image of the inside of the measurement target 10. Thus, it is possible to configure the measurement apparatus 100 to be capable of acquiring information about the inside of the measurement target 10 at high speed while utilizing existing equipment or the like.

By using the impedance distribution, the measurement apparatus 100 according to the present embodiment can observe a normal state, an abnormal state, and the like of an organ which has been difficult to observe with MRI. In such observation of the internal state of the human body, it is desirable to be able to more accurately measure a minute portion. Therefore, the measurement apparatus 100 may be configured such that a current can be directly supplied to the measurement target 10 by using an electrode pair instead of indirectly supplying a current to the measurement target 10 by using a coil. Due to this, the positional accuracy of the location where the measurement apparatus 100 supplies the current can be improved. The following describes such a measurement apparatus 100.

<Second Configuration Example of the Measurement Apparatus 100, and Measurement of Whether the Measurement Target is Normal or Abnormal>

Figure 6:
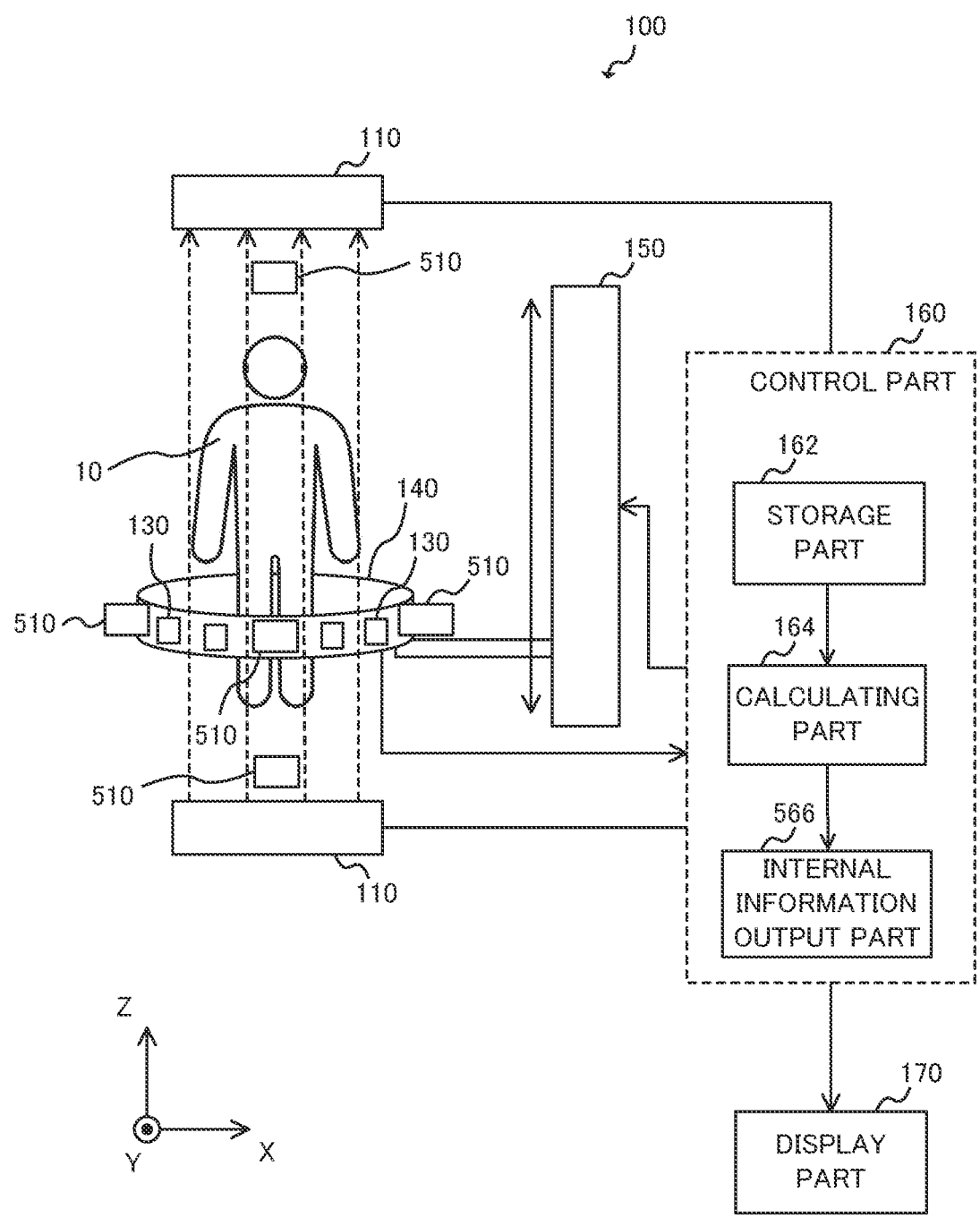
FIG. 6 shows a second configuration example of the measurement apparatus 100 according to the present embodiment, together with the measurement target 10.

FIG. 6 shows a second configuration example of the measurement apparatus 100 according to the present embodiment, together with the measurement target 10. In the measurement apparatus 100 of the second configuration example, components that are substantially the same as those of the measurement apparatus 100 of the first configuration example shown in FIG. 1 are denoted by the same reference numerals, and description thereof is omitted. The measurement apparatus 100 of the second configuration example outputs information about the state of the inside of the measurement target 10. For example, the measurement apparatus 100 applies a current to a human body to which a static magnetic field is applied, and acquires information such as a normal state and an abnormal state of an organ of the human body based on a magnetic field generated in response to the application of the current.

The measurement apparatus 100 includes the static magnetic field applying part 110, a current applying part 510, the magnetic field detecting element 130, the mounting part 140, the moving part 150, the control part 160, and the display part 170. In other words, the measurement apparatus 100 of the second configuration example includes the current applying part 510 instead of the deflection magnetic field applying part 120 of the measurement apparatus 100 of the first configuration example. Since the operation of the static magnetic field applying part 110 is the same as that described with reference to FIG. 1, the description thereof is omitted here.

The current applying part 510 applies an AC current to the human body serving as the measurement target 10, via the electrode pair. The electrode pair is connected to an AC power source, for example, and generates an electric field corresponding to the AC power supplied from the AC power source. The operation of the AC power source is desirably controlled by the control part 160. The electrode pair has a positive electrode and a negative electrode formed separated from each other by a predetermined distance. The shapes of the positive electrode and the negative electrode may be such that an AC current can be supplied to a location to be observed in the measurement target 10. The positive electrode and the negative electrode are preferably disposed in the vicinity of the measurement target 10 so that an AC current can be supplied to the location to be observed in the measurement target 10, and may be disposed in contact with the measurement target 10.

The current applying part 510 includes one or more electrode pairs. It is desirable that the current applying part 510 can apply a plurality of AC currents corresponding to eddy currents generated by a plurality of deflection magnetic fields oriented in a plurality of directions different from the first direction to a portion of the measurement target 10. At least six current applying parts 510 are provided so that AC current can be applied in six directions, which are the +X direction, the +Y direction, and the +Z direction, for example. The current applying part 510 is desirably disposed so as to be able to apply AC currents of various magnitudes and directions to arbitrary locations in the measurement target 10. Further, each of the current applying parts 510 may be movable so as to apply an AC current to various locations in the measurement target 10.

The AC current applied by the current applying part 510 is a current corresponding to an eddy current generated by a deflection magnetic field in a second direction different from the first direction in a portion of the measurement target 10. In other words, the current applying part 510 applies a current similar to the eddy current generated by the deflection magnetic field applied by the deflection magnetic field applying part 120 shown in FIG. 1 to the localized portion of the measurement target 10. Due to this, a magnetic field corresponding to the AC current corresponding to the impedance of the localized portion is generated in the localized portion of the measurement target 10. The waveform of the AC current may be a sine wave, a triangular wave, a rectangular wave, or the like, or may be a pulse wave, an attenuated wave, a burst wave, or the like.

The magnetic field detecting element 130 detects the magnitude of the magnetic field generated in this manner. The magnetic field detecting element 130 of the second configuration example detects the magnitude of the magnetic field generated from a portion of the measurement target 10 in accordance with the AC current supplied from the current applying part 510. One or more magnetic field detecting elements 130 are provided in the vicinity of the measurement target 10. For example, as described above, it is desirable that a plurality of magnetic field detecting elements 130 are disposed around the measurement target 10 to surround the measurement target 10. It is desirable that a plurality of magnetic field detecting elements 130 are provided so as to be able to detect magnetic fields in a plurality of directions. Due to this, the magnetic field detecting elements 130 can detect the magnitude of the magnetic field corresponding to the impedance of the organ or the like in the human body, which is the measurement target 10, for example.

The mounting part 140 has a plurality of current applying parts 510 mounted thereon. As described above, the mounting part 140 has a ring shape or a partial ring shape surrounding the measurement target 10. Further, at least some of the plurality of magnetic field detecting elements 130 may be mounted on the mounting part 140. The moving part 150 moves the mounting part 140 in a predetermined direction while maintaining the direction of the AC current generated by the one or more current applying parts 510 with respect to the measurement target 10. The other operations of the mounting part 140 and the moving part 150 are the same as those already described with reference to FIG. 1, and so description thereof is omitted here.

The control part 160 controls operations of the static magnetic field applying part 110, the current applying part 510, the magnetic field detecting element 130, the mounting part 140, and the moving part 150. The control part 160 controls the application timing of the static magnetic field by the static magnetic field applying part 110 and the application timing of the AC current by the current applying part 510, for example. Further, the control part 160 may control the application direction of the AC current.

During a period in which the static magnetic field is applied from the static magnetic field applying part 110 to the measurement target 10, the control part 160 applies an AC current from the current applying part 510 to the measurement target 10. Due to this, the AC current is applied in a state in which the measurement target 10 is macroscopically magnetized. Therefore, in the same manner as in the MRI operation, the rotational speed of the precession of the atoms to which the AC current is applied among the atoms forming the measurement target 10 changes. Due to such a change in the precession, an electromagnetic wave in a state differing from the steady state is generated from the atoms to which the AC current is applied.

As an example, the control part 160 applies an AC current to a location in the measurement target 10, and acquires a detection result of the magnetic field detecting element 130 corresponding to the location at which the AC current is applied. In this way, the control part 160 can acquire the detection result of the magnetic field corresponding to the impedance of the location at which the AC current is applied in the measurement target 10. Further, the control part 160 applies an AC current to a plurality of locations in the measurement target 10, and acquires the detection result of the magnetic field detecting element 130 for each location at which the AC current is applied, for example. In this way, the control part 160 can acquire the detection result of the magnetic field corresponding to the impedance, the impedance distribution, and the like inside the measurement target 10.

By analyzing such a detection result, the control part 160 can generate information about the state of the inside of the measurement target 10. The control part 160 includes the storage part 162, the calculating part 164, and an internal information output part 566, for example. Since the operations of the storage part 162 and the operation of the calculating part 164 are the same as those already described with reference to FIG. 1, the description thereof is omitted here. The calculating part 164 may calculate the impedance inside the measurement target 10 based on the detection result of the magnetic field detecting element 130 at one location inside the measurement target 10.

The internal information output part 566 generates and outputs information indicating the state of the inside of the measurement target 10 based on the impedance and/or the impedance distribution calculated by the calculating part 164. The internal information output part 566 can generate information indicating a state of a wider area by using the impedance distribution. In this case, the internal information output part 566 may generate and output an image based on the impedance distribution. The internal information output part 566 generates information such as an abnormal state caused by a tumor such as cancer occurring in an organ or the like. Further, the internal information output part 566 generates information in which an organ or the like is in a normal state in response to being unable to detect an abnormal state. The display part 170 displays information indicating the state of the inside of the measurement target 10 generated by the internal information output part 566.

As described above, the measurement apparatus 100 of the second configuration example can efficiently measure the state of the inside of the living body such as a human body by supplying the AC current to the location to be observed. Here, in the measurement apparatus 100 of the second configuration example, similarly to the measurement apparatus 100 of the first configuration example, the static magnetic field applying part 110 may change the magnitude of the static magnetic field applied to the measurement target 10, and the impedance may be calculated for each magnitude of the static magnetic field.

Similarly to the measurement apparatus 100 of the first configuration example, the measurement apparatus 100 of the second configuration example described above can calculate the impedance without observing the relaxation phenomenon occurring until the nuclear magnetic resonance phenomenon returns to the steady state, and can therefore output the measurement result at high speed. Further, the magnetic field detecting element 130 can measure the state of the inside of the measurement target 10 while being small-scale and inexpensive, by using the highly sensitive magnetic sensor listed in Patent Document 1 or 2.

Also in the measurement apparatus 100 of the second configuration example, when a highly sensitive magnetic sensor capable of detecting weak magnetic fields in units of picoteslas or less is used as the magnetic field detecting element 130, the magnitude of the static magnetic field output from the static magnetic field applying part 110 can be made smaller. For example, even if the magnitude of the static magnetic field output from the static magnetic field applying part 110 is reduced to a magnitude of several hundred times the magnitude of geomagnetism, the state inside the measurement target 10 can be measured.

In the measurement apparatus 100 of the second configuration example described above, an example of detecting the magnetic field based on the application of the AC current has been described, but the present disclosure is not limited thereto. The measurement apparatus 100 may cause a nuclear magnetic resonance phenomenon in the measurement target 10 and observe the relaxation phenomenon occurring until the nuclear magnetic resonance phenomenon returns to a steady state, such as in MRI. For example, the measurement apparatus 100 is configured to directly supply a current to the measurement target 10 by using the electrode pair, and can therefore generate the nuclear magnetic resonance phenomenon.

In this case, a plurality of current applying parts 510 are provided around the measurement target 10 and apply a plurality of AC currents oriented in a plurality of directions, toward a portion of the measurement target 10. The magnetic field detecting element 130 detects the relaxation phenomenon of the magnetic field based on the plurality of AC currents generated by the plurality of current applying parts 510 in a portion of the measurement target 10. The calculating part 164 calculates the impedance inside the measurement target 10 in time series. Due to this, the internal information output part 566 can generate and output an image corresponding to the magnetic resonance image indicating information about the inside of the measurement target 10 based on the calculated change in impedance.

In this case, the internal information output part 566 can generate an image corresponding to the magnetic resonance image of the measurement target 10 by performing known signal processing on the change in impedance, for example. If the detection sensitivity of the magnetic field detecting element 130 is sufficiently high, the internal information output part 566 can output an image, corresponding to the magnetic resonance image, that is approximately equal to the magnetic resonance image. The display part 170 may display an image corresponding to the magnetic resonance image generated by the internal information output part 566, and may display information indicating the internal state together with the image.

Alternatively or in addition to this, the measurement apparatus 100 may further include a member for capturing a magnetic resonance image. The following describes such a measurement apparatus 100.

<Modified Example of the Measurement Apparatus 100 of the Second Configuration Example, Generation of an MR Image, and Measurement Apparatus of the First Configuration Example>

Figure 7:
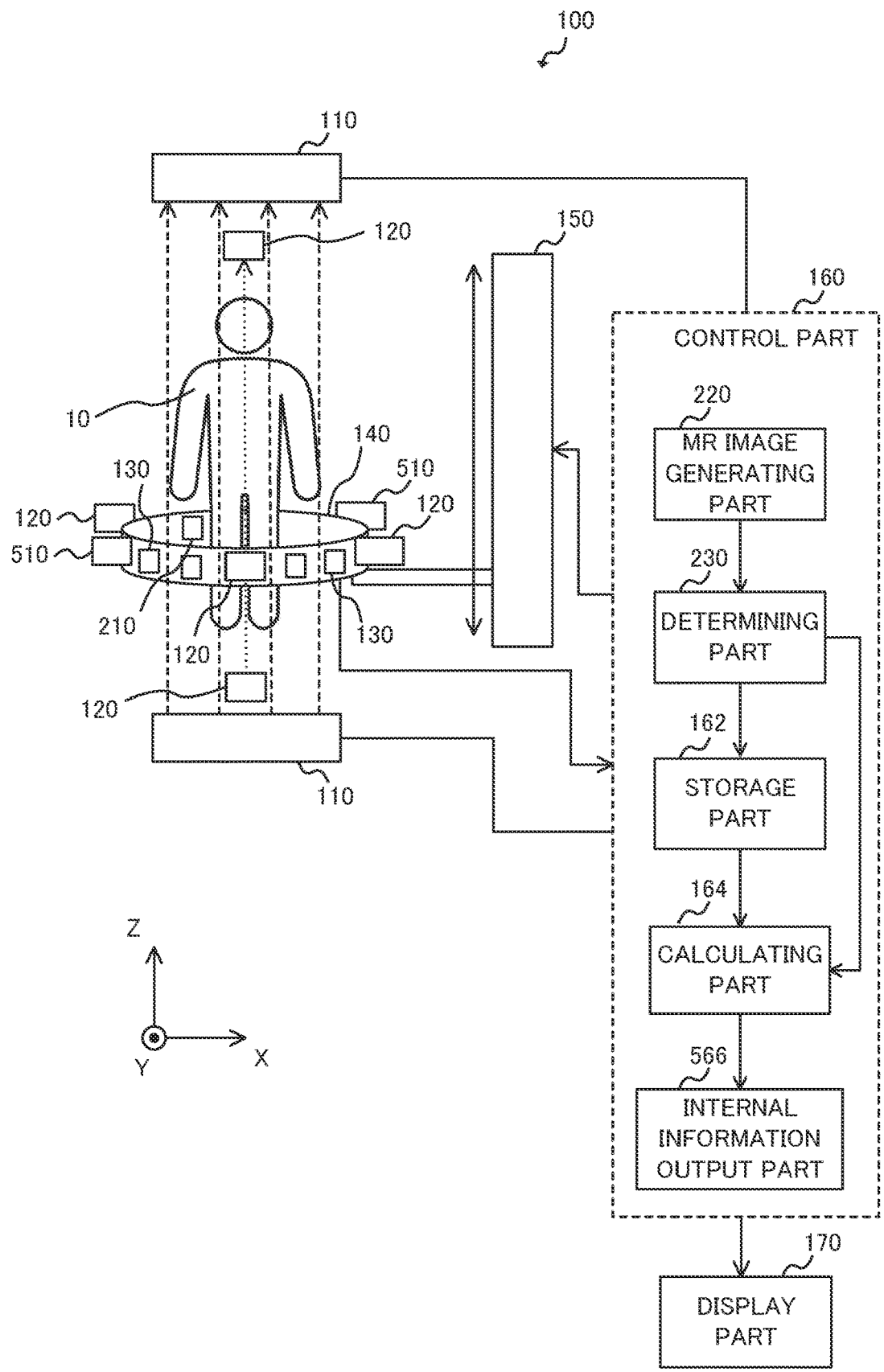
FIG. 7 shows a modified example of the measurement apparatus 100 of the second configuration example according to the present embodiment, together with the measurement target 10.

FIG. 7 shows a modified example of the measurement apparatus 100 of the second configuration example according to the present embodiment, together with the measurement target 10. In the measurement apparatus 100 according to the present modification, components that are substantially the same as those of the measurement apparatus 100 according to the second configuration example shown in FIG. 6 are denoted by the same reference numerals, and description thereof is omitted. The measurement apparatus 100 of this modification includes the deflection magnetic field applying part 120, the relaxation detecting element 210, the MR image generating part 220, and the determining part 230.

The deflection magnetic field applying part 120 has a predetermined frequency and applies a deflection magnetic field in a second direction, which is different from the first direction, toward a portion of the measurement target 10 via a coil. The deflection magnetic field applying part 120 includes a plurality of magnetic field generating coils, and applies a plurality of deflection magnetic fields oriented in a plurality of directions that are different from the first direction toward a portion of the measurement target 10. Since the operations of the deflection magnetic field applying part 120, the relaxation detecting element 210, and the MR image generating part 220 are the same as the operations of these parts described in the modified example of the measurement apparatus 100 of the first configuration example, description thereof is omitted here.

In this way, the measurement apparatus 100 is configured to be capable of measuring the internal information of the measurement target 10 using the AC current and of measuring the magnetic resonance image. In this case, the measurement apparatus 100 is desirably configured to be capable of switching between the measurement of the internal information of the measurement target 10 and the measurement of the magnetic resonance image. Further, it is more preferable that the measurement location of the internal information in the measurement target 10 can be specified based on the measurement result of the magnetic resonance image. In this case, the control part 160 includes the determining part 230.

Based on the magnetic resonance image generated by the MR image generating part 220, the determining part 230 determines a location in the measurement target 10 at which the AC current is to be applied by the current applying part 510. The magnetic resonance image can display information of a position inside the measurement target 10 with high spatial resolution. Therefore, the determining part 230 can easily determine the location of an organ in the body to be observed, for example.

The determining part 230 determines a location where an abnormality is estimated to be in the magnetic resonance image as a location at which an AC current is to be applied, based on image processing such as image analysis and image comparison. Alternatively, after the magnetic resonance image is displayed on the display part 170, the determining part 230 may receive an input of a location at which the AC current is to be applied from a user or the like. The following describes such an operation of the measurement apparatus 100.

<Second Example of the Operation Flow of the Measurement Apparatus 100>

Figure 8:
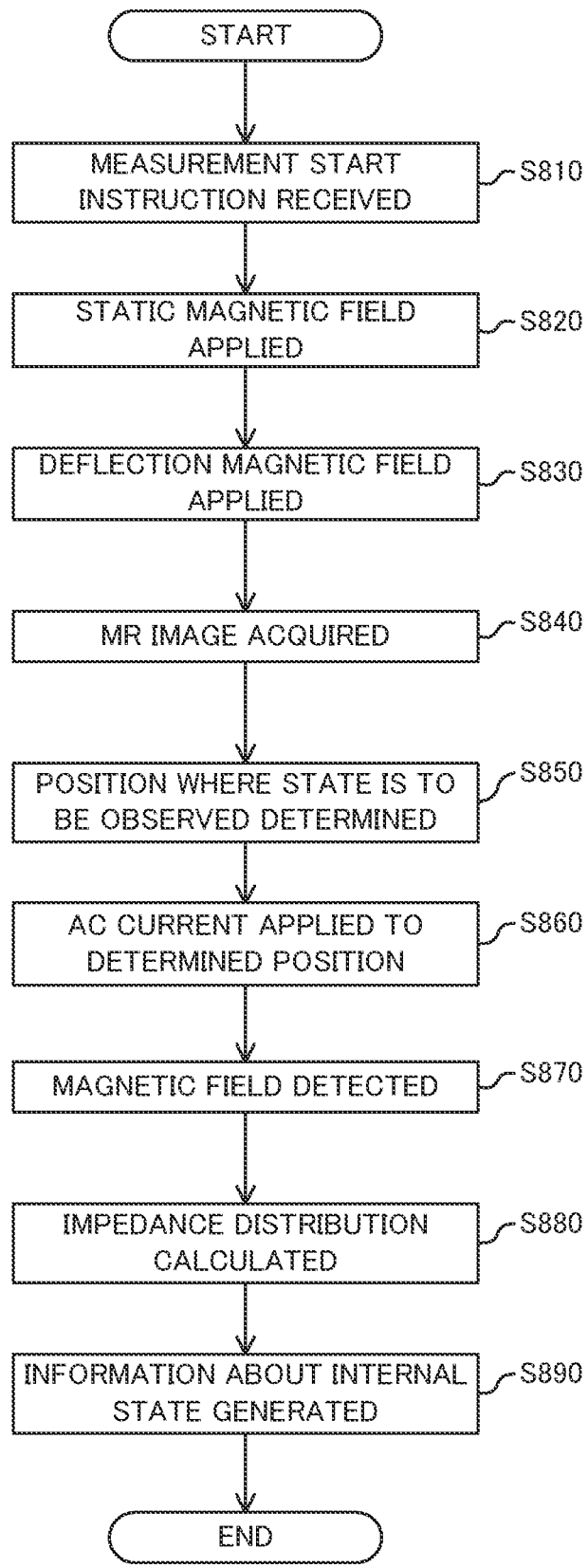
FIG. 8 shows an example of an operation flow of the measurement apparatus 100 of the present modification shown in FIG. 7.

FIG. 8 shows an example of an operation flow of the measurement apparatus 100 of the present modification shown in FIG. 7. The measurement apparatus 100 outputs information on the internal state of the measurement target 10 by executing the operation flow from S810 to S890.

First, the control part 160 receives a measurement start instruction for the measurement target 10 from a user or the like (S810). Here, it is assumed that the measurement target 10 is disposed so as to have a predetermined positional relationship with respect to the static magnetic field applying part 110, the deflection magnetic field applying part 120, the magnetic field detecting element 130, and the current applying part 510. The control part 160 further receives information concerning the measurement range of the measurement target 10. The control part 160 receives an instruction of a measurement range such as a head, a neck, a chest, an abdomen, a waist, a leg, the whole body, or the like. In accordance with the received information, the control part 160 controls the moving part 150 to move the mounting part 140 to the measurement start point of the measurement range.

Next, the static magnetic field applying part 110 applies a static magnetic field having a constant magnitude in the first direction to the measurement target 10 (S820). The static magnetic field applying part 110 applies a static magnetic field having a predetermined intensity level to the measurement target 10.

Next, the deflection magnetic field applying part 120 applies a deflection magnetic field that has a predetermined frequency and is oriented in a second direction, which is different from the first direction, to a location in the measurement target 10 to be observed (S830). The deflection magnetic field applying part 120 applies a deflection magnetic field to a portion of the measurement target 10 corresponding to the received measurement range.

Next, the control part 160 acquires and outputs a magnetic resonance image of the measurement range of the measurement target 10 (S840). The relaxation detecting element 210 detects the electromagnetic wave generated by the application of the deflection magnetic field and the relaxation phenomenon of the generated electromagnetic wave in the measurement range of the measurement target 10. The MR image generating part 220 generates and outputs a magnetic resonance image, which is a tomographic image of the inside of the measurement target, based on the detection results of the generated electromagnetic wave and the relaxation phenomenon of the electromagnetic wave. The MR image generating part 220 displays the generated magnetic resonance image on the display part 170, for example.

Next, based on the magnetic resonance image, the determining part 230 determines the internal position in the measurement target 10 to be observed (S850). The determining part 230 receives an input of a location to be observed from a user of the measurement apparatus 100 who has confirmed the magnetic resonance image of the measurement target 10 displayed on the display part 170, for example. Further, the determining part 230 may determine a location where the state is to be observed by image analysis.

Next, the current applying part 510 applies an AC current toward the determined position inside the measurement target 10 (S860). Then, the plurality of magnetic field detecting elements 130 respectively detect magnitudes of magnetic fields generated in a portion of the measurement target 10 due to the application of the AC current, around the measurement target 10 (S870).

Next, the calculating part 164 calculates the impedance inside the measurement target 10 based on the detection result of the magnetic field (S880). The internal information output part 566 generates and outputs information about the internal state of the measurement target 10 based on the impedance (S890). The internal information output part 566 generates information such as whether an organ is normal, abnormal, or suspected to be abnormal. The internal information output part 566 displays the generated information on the display part 170. For example, the display part 170 displays the internal state at a position corresponding to the measured organ in the magnetic resonance image.

As described above, the measurement apparatus 100 according to the present modified example determines the location where the internal state of the measurement target 10 is to be acquired, based on the magnetic resonance image. Due to this, the measurement apparatus 100 can appropriately determine the location to be observed using the positional information of the measurement target 10 measured with high spatial resolution, and can quickly measure the internal state.

The operation flow described with reference to FIG. 8 is an example of the operation flow of the measurement apparatus 100 provided with the static magnetic field applying part 110, but is not limited thereto. When the measurement apparatus 100 measures an image inside the measurement target 10 and a magnetic resonance image using geomagnetism, for example, the operation of S820 by the static magnetic field applying part 110 may be omitted. Further, the measurement apparatus 100 may measure the magnetic resonance image after measuring the internal state.

Further, instead of the deflection magnetic field, the measurement apparatus 100 may generate an image corresponding to the magnetic resonance image by applying an AC current to the measurement target 10 as described above. In this case, the operation of S830 is, for example, an operation in which the plurality of current applying parts 510 apply a plurality of AC currents oriented in a plurality of directions, from a plurality of positions around the measurement target 10, toward a portion of the measurement target 10.

In the operation of S840, the relaxation detecting element 210 detects a relaxation phenomenon of a magnetic field generated based on the plurality of AC currents in a portion of the measurement target 10. Then, the internal information output part 566 generates and outputs an image corresponding to a magnetic resonance image indicating information about the inside of the measurement target 10 based on the change in impedance calculated by the calculating part 164.

In the operation of S850, the determining part 230 determines a location in the measurement target 10 to which the AC current corresponding to the eddy current generated by the deflection magnetic field in the second direction is to be applied, based on the image corresponding to the magnetic resonance image. In this way, the determining part 230 may determine a location in the measurement target 10 where the state is to be measured by applying the AC current, based on the image corresponding to the magnetic resonance image.

<Combination of the First Configuration Example and Second Configuration Example>

Further, the measurement apparatus 100 may be configured to be capable of quickly measuring an image of the inside of the measurement target 10 as described with the measurement apparatus 100 of the first configuration example. In this case, the control part 160 is further provided with the image information output part 166 that generates and outputs an image indicating information about the inside of the measurement target 10. Then, the plurality of magnetic field detecting elements 130 respectively detect the magnitudes of magnetic fields based on electromagnetic waves generated and propagated in a portion of the measurement target 10 due to the application of the deflection magnetic field by the deflection magnetic field applying part 120.

Then, based on the detection results of the plurality of magnetic field detecting elements 130, the calculating part 164 calculates the impedance distribution of at least a portion of the region where the electromagnetic wave propagates inside the measurement target 10. Thus, the image information output part 166 generates an image indicating information about the inside of the measurement target 10, based on the impedance distribution calculated by the calculating part 164.

As described in steps S410 to S480 of FIG. 4, the measurement apparatus 100 can quickly measure a tomographic image of the impedance distribution of the measurement target 10 and determine a measurement range in which the magnetic resonance image is to be observed. Then, as described in steps S830 to S850 of FIG. 8, the measurement apparatus 100 can determine a location where an internal state is to be observed by observing a magnetic resonance image. As a result, the measurement apparatus 100 can appropriately determine the internal position in the measurement target 10 to be observed and quickly measure the internal state, as described in S860 to S890 of FIG. 8.

If the measurement apparatus 100 does not require a spatial resolution high enough to use a magnetic resonance image, the determining part 230 may determine the internal position to be observed based on the tomographic image of the impedance distribution of the measurement target 10. The measurement apparatus 100 can measure the internal state of the measurement target 10 at a higher speed without using a magnetic resonance image. The measurement apparatus 100 may be configured for such purposes, and in this case, the relaxation detecting element 210 and the MR image generating part 220 need not be provided. In this case, the measurement apparatus 100 has the function of the first configuration example described in FIG. 1 and the function of the second configuration example described in FIG. 6.

<Configuration Example of the Detection Apparatus 600 and Configuration Added to the MR Image Measurement Apparatus>

Figure 9:
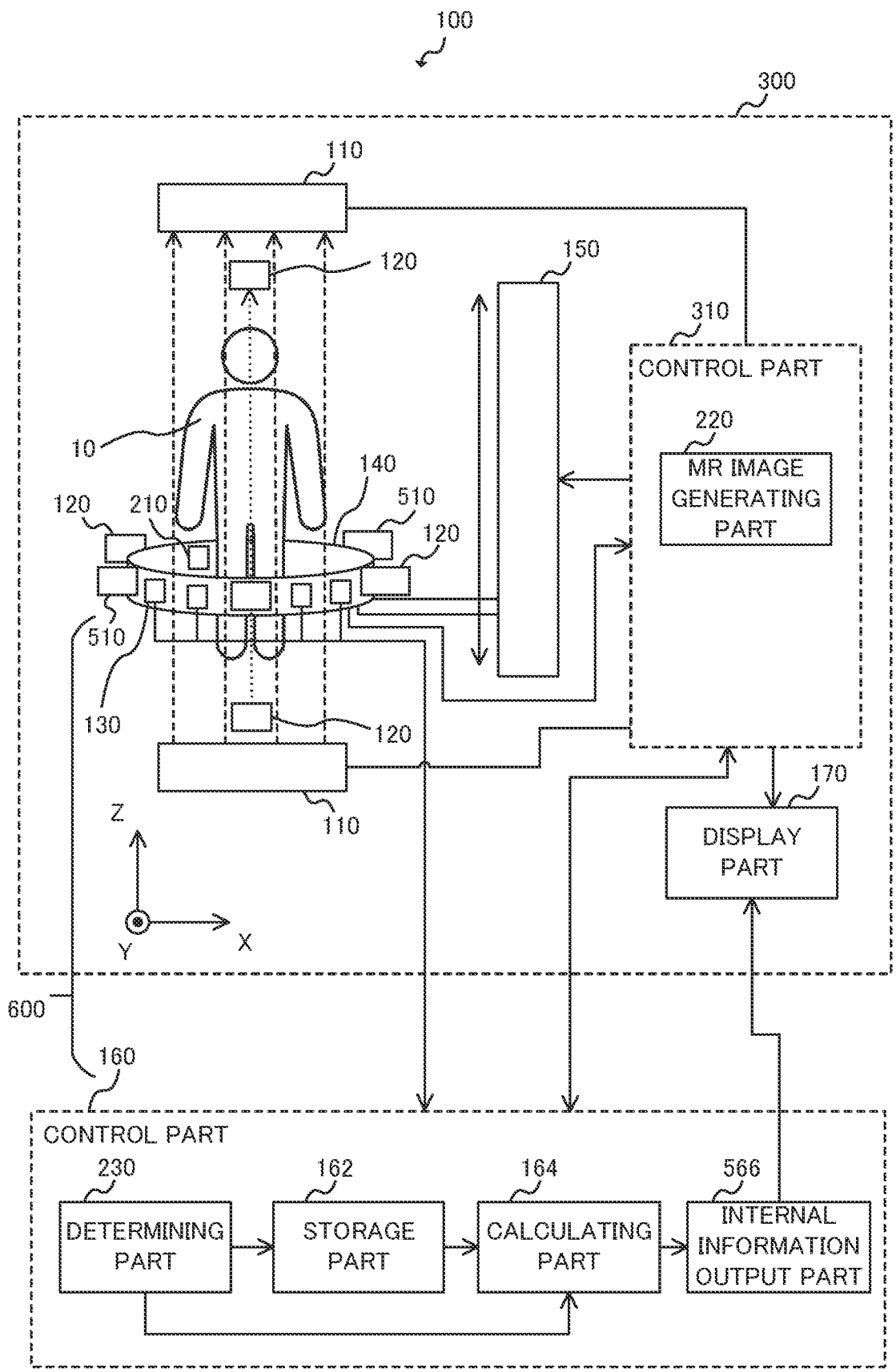
FIG. 9 shows a configuration example of a detection apparatus 600 according to the present embodiment, together with the MR image measurement apparatus 300.

Although the measurement apparatus 100 of the second configuration example has been described as an independent apparatus, the present disclosure is not limited thereto. The measurement apparatus 100 may be an apparatus that functions by being added to an existing MR image measurement apparatus that outputs a magnetic resonance image, similarly to the detecting apparatus 400 described with reference to FIG. 5. FIG. 9 shows a configuration example of the detection apparatus 600 according to the present embodiment, together with the MR image measurement apparatus 300.

The MR image measurement apparatus 300 includes at least a configuration that operates in the same manner as the static magnetic field applying part 110, the deflection magnetic field applying part 120, the mounting part 140, the moving part 150, the display part 170, the relaxation detecting element 210, and the MR image generating part 220 according to the present embodiment. The MR image measurement apparatus 300 includes the control part 310 that controls each part in order to measure a magnetic resonance image. Since the measurement of the magnetic resonance image by the MR image measurement apparatus 300 is substantially the same as the operation described above, description thereof is omitted here.

The detection apparatus 600 is provided in such an MR image measurement apparatus 300. In this case, a combination of the MR image measurement apparatus 300 and the detecting apparatus 600 functions as at least a portion of the measurement apparatus 100 according to the present embodiment. The detection apparatus 600 includes the current applying part 510, a plurality of the magnetic field detecting elements 130, and the control part 160 including the storage part 162, the calculating part 164, the determining part 230, and the internal information output part 566.

The detection apparatus 600 transmits and receives a control signal or the like to and from the MR image measurement apparatus 300 to generate and output information indicating the internal state of the measurement target 10. Further, the detection apparatus 600 receives the magnetic resonance image generated by the MR image measurement apparatus 300, and determines a position at which the internal state of the measurement target 10 is to be observed. Then, the detection apparatus 600 supplies a control signal instructing application of the AC current to the MR image measurement apparatus 300 based on the determined observation position for the internal state. Due to this, it is possible to configure the measurement apparatus 100 to be capable of acquiring the internal state of the measurement target 10 at high speed while utilizing existing equipment or the like.

In the measurement apparatus 100 of the second configuration example, an example has been described in which the abnormal state and the normal state of the measurement target 10 can be determined by applying the AC current to the measurement target 10 to which the static magnetic field is applied. It has been described that the location measured by the measurement apparatus 100 may be determined based on an image generated by the measurement apparatus 100 or the MR image measurement apparatus 300 of the first configuration example, but the present disclosure is not limited to this. If the apparatus is capable of outputting the inside of the measurement target 10 as an image, the measurement apparatus 100 can determine the location to be measured.

For example, the measurement apparatus 100 may be combined with a device that outputs the inside of the measurement target 10 as an image by applying AC current oriented in a plurality of directions. Further, since the measurement apparatus 100 may be configured to include the current applying part 510 for applying the AC current to the measurement apparatus 100, the measurement apparatus 100 can have such a function. The following describes an apparatus having such a function.

<Third Configuration Example of the Measurement Apparatus 100, and Measurement of an Internal Image of the Measurement Target by Applying a Current>

Figure 10:
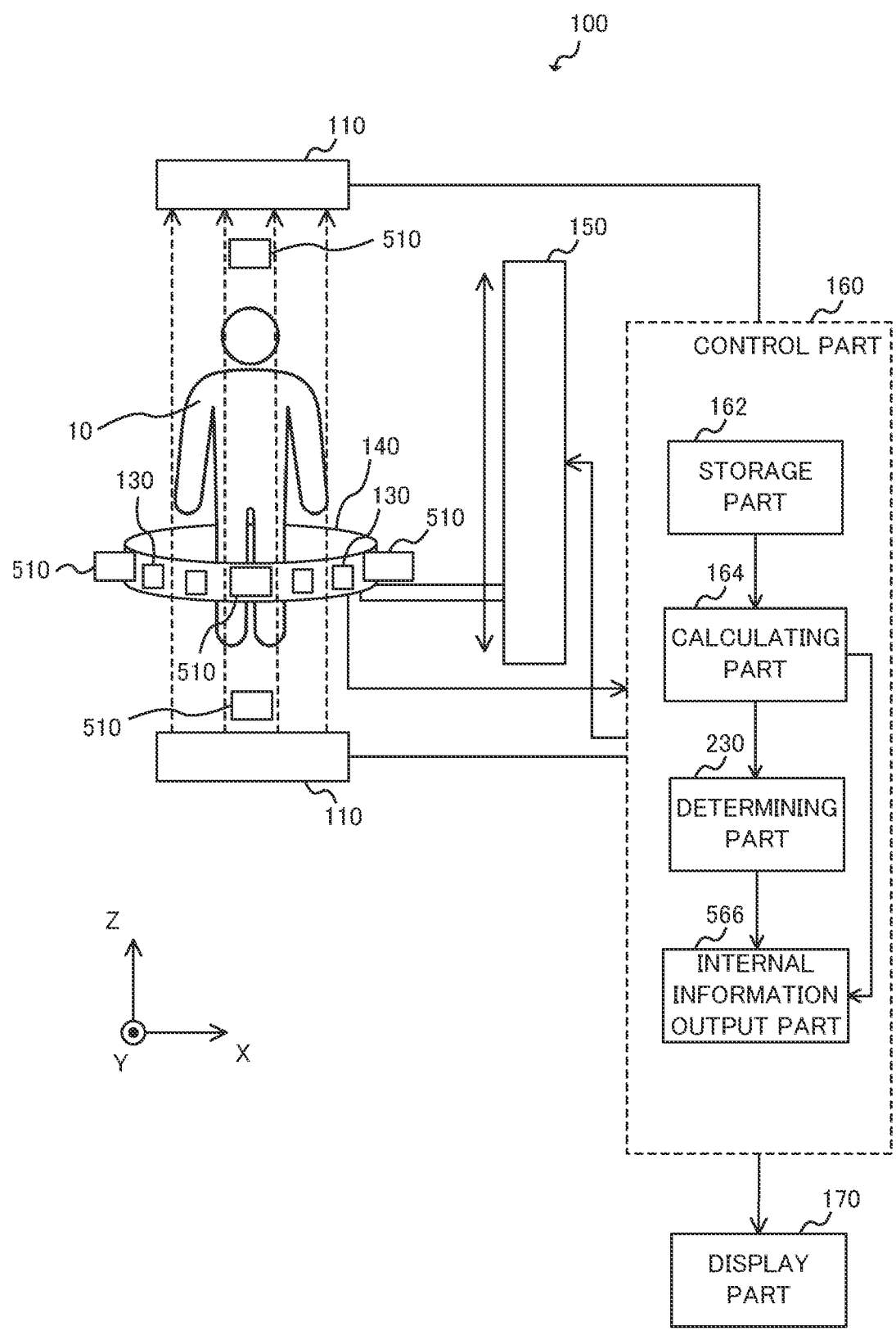
FIG. 10 shows a third configuration example of the measurement apparatus 100 according to the present embodiment, together with the measurement target 10.

FIG. 10 shows a third configuration example of the measurement apparatus 100 according to the present embodiment, together with the measurement target 10. The measurement apparatus 100 of the third configuration example applies an AC current to the measurement target 10 without applying a static magnetic field to the measurement target 10, and outputs the inside of the measurement target 10 as an image. As described above, the measurement apparatus 100 determines the abnormal state and the normal state of the measurement target 10 by applying the static magnetic field and the AC current to the measurement target 10.

The measurement apparatus 100 includes the static magnetic field applying part 110, the magnetic field detecting element 130, the mounting part 140, the moving part 150, the control part 160, the display part 170, the determining part 230, and the current applying part 510. In other words, the measurement apparatus 100 of the third configuration example has substantially the same configuration as the measurement apparatus 100 of the second configuration example, and components that are substantially the same as those of the measurement apparatus 100 of the second configuration example shown in FIG. 6 are denoted by the same reference numerals and description thereof is omitted.

A plurality of current applying parts 510 are provided around the measurement target. The current applying parts 510 apply a plurality of AC currents oriented in a plurality of directions, toward a portion of the measurement target 10. A plurality of the magnetic field detecting elements 130 are disposed around the measurement target 10, and each of the magnetic field detecting elements 130 detects the magnitude of a magnetic field generated from a portion of the measurement target 10 according to the plurality of applied AC currents. In this case, the calculating part 164 calculates the impedance distribution inside the measurement target based on the detection results of the plurality of magnetic field detecting elements 130.

When the static magnetic field is not being applied to the measurement target 10, the impedance distribution calculated by the calculating part 164 is an impedance distribution corresponding to a line of electric force generated by the application of the AC current to the inside of the measurement target 10. When the calculating part 164 calculates the impedance distribution by applying the AC currents to the inside of the measurement target 10 from a plurality of directions, the impedance distribution corresponding to the internal structure of the measurement target 10 can be acquired.

Accordingly, the internal information output part 566 can generate and output an image indicating the information about the inside of the measurement target 10, based on the calculated impedance distribution. The internal information output part 566 generates a tomographic image of a portion of the measurement target 10 by processing the impedance distribution using a known numerical analysis or the like, for example. In this way, the measurement apparatus 100 of the third configuration example can output a tomographic image of the measurement target 10 at a higher speed and more simply than an MR measurement apparatus or the like.

At least some of the current applying parts 510 may sweep the frequency of the AC current applied to the measurement target 10. In this case, the calculating part 164 can calculate the frequency characteristic of the impedance corresponding to the frequency of the AC current. The internal information output part 566 can then generate the internal state of the measurement target 10 based on the frequency characteristic of the impedance.

Inside the measurement target 10, an induction magnetic field is generated in response to the applied AC current. The frequency of the generated induction magnetic field corresponds to the frequency of the applied AC current. Therefore, when the frequency of the AC current is swept while the location at which the AC current is applied is fixed, a spectrum distribution of the induction magnetic field generated can be acquired. The spectrum distribution of the induction magnetic field is a spectrum distribution corresponding to an organ or the like of the human body, for example.

Therefore, by analyzing the spectrum distribution of the induction magnetic field, the organ at the location where the AC current is applied can be distinguished. The spectrum distribution of the induction magnetic field can be different between normal cells and abnormal cells, even in the same organ. Accordingly, based on the spectrum distribution of the induction magnetic field, it is possible to determine whether or not the organ at the location where the AC current is applied is normal. As an example, the internal information output part 566 compares the acquired spectrum distribution with the spectrum distribution of a normal organ measured in the past, to determine whether or not the location where the AC current is applied is normal.

The determining part 230 determines a location in the measurement target 10 at which the state is to be detected by applying the AC current with the current applying part 510, based on the image indicating the internal information of the measurement target 10 generated by the internal information output part 566. For example, the determining part 230 receives information of a location to be detected from a user of the measurement apparatus 100. Here, the user can determine the location to be detected from an image inside the measurement target 10 including information of the organ. Then, the measurement apparatus 100 measures the state at the determined location by applying the static magnetic field and the AC current to the determined location as described with reference to FIG. 6, for example.

<Example of an Operation Flow of the Measurement Apparatus 100 of the Third Configuration Example>

Figure 11:
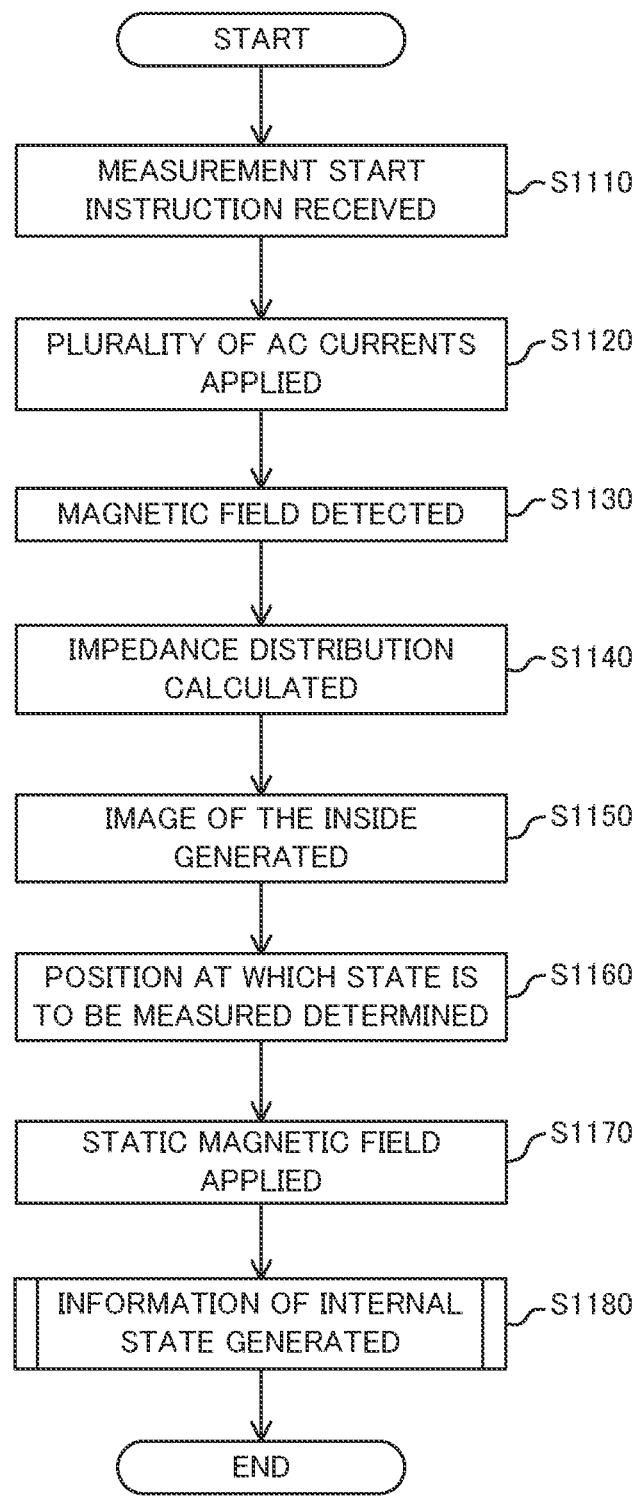
FIG. 11 shows an example of an operation flow of the measurement apparatus 100 of the third configuration example.

FIG. 11 shows an example of an operation flow of the measurement apparatus 100 of the third configuration example. The measurement apparatus 100 outputs information about the internal state of the measurement target 10 by executing the operation flow from S1110 to S1180.

First, the control part 160 receives a measurement start instruction for the measurement target 10 from a user or the like (S1110). Here, it is assumed that the measurement target 10 is disposed so as to have a predetermined positional relationship with respect to the static magnetic field applying part 110, the magnetic field detecting element 130, and the current applying part 510. The control part 160 further receives information about the measurement range of the measurement target 10. The control part 160 receives an instruction for a measurement range such as a head, a neck, a chest, an abdomen, a waist, a leg, the whole body, or the like. In accordance with the received information, the control part 160 controls the moving part 150 to move the mounting part 140 to the measurement start point of the measurement range.

Next, the plurality of current applying parts 510 apply AC currents in a plurality of directions toward the determined position inside the measurement target 10 (S1120). The plurality of magnetic field detecting elements 130 detect the magnitudes of magnetic fields generated in a portion of the measurement target 10 due to the application of the AC currents, around the measurement target 10 (S1130). The plurality of current applying parts 510 apply the plurality of AC currents one by one to the measurement target 10 in a predetermined order, for example. In this case, the application of the current in S1120 and the detection of the magnetic field in S1130 may be repeated. Further, at least some of the current applying parts 510 among the plurality of current applying parts 510 may sweep the frequency of the AC current applied to the measurement target 10.

Next, the calculating part 164 calculates the impedance distribution inside the measurement target 10 based on the detection result of the magnetic field (S1140). The internal information output part 566 generates and outputs an image indicating information about the inside of the measurement target 10, based on the impedance distribution (S1150). By executing the operation flow from S1110 to S1150 a plurality of times, images of a plurality of locations may be acquired.

Next, the determining part 230 determines a location in the measurement target 10 at which the state is to be observed by applying the AC current with the current applying part 510, based on the image of the inside of the measurement target 10 generated by the internal information output part 566 (S1160). For example, the determining part 230 receives an input of a location to be observed from a user of the measurement apparatus 100 who has confirmed an image of the inside of the measurement target 10 displayed on the display part 170. Further, the determining part 230 may determine a location where the state is to be observed, by using image analysis.

Next, the static magnetic field applying part 110 applies a static magnetic field having a constant magnitude in the first direction to the measurement target 10 (S1170). The static magnetic field applying part 110 applies a static magnetic field having a predetermined intensity level to the measurement target 10. Then, the measurement apparatus 100 generates and outputs information about the internal state of the measurement target 10 (S1180). Note that since the operation of S1180 is the same as the operations of S860 to S890 described with reference to FIG. 8, description thereof is omitted here.

In the manner described above, the measurement apparatus 100 according to the third configuration example determines the location where the internal state of the measurement target 10 is to be measured, based on the image of the inside of the measurement target 10 acquired by applying the AC current in a plurality of directions. Thus, the measurement apparatus 100 can appropriately determine the location to be observed using the positional information of the measurement target 10 measured with high spatial resolution, and can quickly measure the internal state.

The measurement apparatus 100 of the third configuration example may measure the internal state of the measurement target 10 by sweeping the frequency of the AC current applied to the measurement target 10 by the current applying part 510. In this case, the measurement apparatus 100 does not perform the operation of S1170, and applies the AC current from the current applying part 510 to the position inside of the measurement target 10 where the state is to be observed, as determined by the determining part 230, thereby sweeping the frequency of the AC current. Then, the calculating part 164 calculates the frequency characteristic of the impedance corresponding to the frequency of the AC current, and the internal information output part 566 generates and outputs the internal state of the measurement target 10 based on the frequency characteristic of the impedance (S1180). In such a measurement apparatus 100, the static magnetic field applying part 110 may be omitted.

As described above, the measurement apparatus 100 can acquire a tomographic image of the inside of the measurement target 10 with a simple configuration in which AC current is applied to the measurement target 10 from a plurality of directions and the generated magnetic field is detected. Thus, the measurement apparatus 100 can determine a location at which the internal state is to be measured in the measurement target 10 based on the acquired tomographic image and measure the state at this location, with a simpler configuration. Further, since the measurement apparatus 100 can acquire the tomographic image of the measurement target 10 and measure the internal state using the common current applying part 510 and magnetic field detecting element 130, the configuration of the apparatus can be simplified and the cost of the apparatus can be reduced.

<Modified example of the Measurement Apparatus 100 of the Third Configuration Example>

The measurement apparatus 100 of the third configuration example described above may be combined with the other configurations described in the measurement apparatus 100 of the first configuration example and the measurement apparatus 100 of the second configuration example. For example, as described with reference to FIG. 7, the measurement apparatus 100 of the third configuration example may further include the deflection magnetic field applying part 120, the relaxation detecting element 210, and the MR image generating part 220, and may have a function of measuring a magnetic resonance image. In this case, the determining part 230 determines a location in the measurement target 10 where the magnetic resonance image is to be measured, based on the internal image of the measurement target 10 generated by the internal information output part 566. Then, based on the magnetic resonance image generated by the MR image generating part 220, the determining part 230 determines a location in the measurement target 10 at which the state is to be detected by applying an AC current with the current applying part 510.

In this case, for example, the measurement apparatus 100 acquires a tomographic image of one or more regions of the measurement target 10 by executing one or more operation flows from S1110 to S1150 in FIG. 11. As an example, the measurement apparatus 100 generates tomographic images at a plurality of different locations in the human body.

Then, the determining part 230 determines a location where a sharper magnetic resonance image is to be measured. As an example, one location where a sharper image is to be obtained is determined from the plurality of tomographic images of the human body. Next, the magnetic resonance image is measured by executing the operation flow from S820 to S840 in FIG. 8. Also, by further executing the operation flow from S850 to S890 in FIG. 8, the state at the location determined from the magnetic resonance image may be measured. Instead of the operations from S860 to S890, the current applying part 510 may sweep the frequency of the AC current applied to the measurement target 10 to measure the state at the location determined from the magnetic resonance image.

As described above, the measurement apparatus 100 can determine the location where the magnetic resonance image is to be measured by easily obtaining more tomographic images at high speed. Then, the measurement apparatus 100 can determine the location at which the state is to be measured, by using a sharp magnetic resonance image.

Further, the measurement apparatus 100 of the third configuration example may be an apparatus that functions by being added to an existing MR image measurement apparatus that outputs a magnetic resonance image, similarly to the detecting apparatus 400 described in FIG. 5 and the detecting apparatus 600 described in FIG. 9. Such a measurement apparatus 100 of the third configuration example has substantially the same configuration as the configuration of FIG. 9. In addition, as described with reference to FIG. 10, such an apparatus applies a plurality of AC currents to output an image of the inside of the measurement target 10.

For example, a plurality of current applying parts 510 are provided around the measurement target 10, and apply a plurality of AC currents oriented in a plurality of directions toward a portion of the measurement target 10. A plurality of magnetic field detecting elements 130 are disposed around the measurement target 10, and detect magnetic fields generated by the application of the plurality of AC currents. The calculating part 164 calculates the impedance distribution inside the measurement target 10 based on the detection results of the plurality of magnetic field detecting elements 130. Then, the internal information output part 566 generates and outputs an image indicating information about the inside of the measurement target 10, based on the calculated impedance distribution.

Further, at least a part of the plurality of current applying parts 510 may sweep the frequency of the AC current applied to the measurement target 10. In this case, the calculating part 164 calculates the frequency characteristic of the impedance corresponding to the frequency of the AC current, and the internal information output part 566 generates information indicating the internal state of the measurement target 10 based on the calculated frequency characteristic of the impedance.

The measurement apparatus 100 of the third configuration example functions as an apparatus combined with the MR image measurement apparatus 300, as described above. Thus, the measurement apparatus 100 can apply a plurality of AC currents to the measurement target 10 to generate an image indicating information about the inside of the measurement target 10. Further, the determining part 230 can determine a location in the measurement target 10 at which the MR image measurement apparatus 300 is to measure the magnetic resonance image, based on the image of the inside of the measurement target 10 generated by the internal information output part 566.

Then, based on the magnetic resonance image generated by the MR image measurement apparatus 300, the determining part 230 can determine the location in the measurement target 10 to be measured by applying the AC current with the current applying part 510. The measurement apparatus 100 can measure the internal state by applying the AC current to the determined position. In this way, it is possible to configure the measurement apparatus 100 to be capable of acquiring an image and a state of the inside of the measurement target 10 at high speed, while utilizing existing equipment or the like.

In the measurement apparatus 100 of the third configuration described above, an example is described in which the measurement apparatus 100 is combined with an apparatus that outputs a sharper MR image, but the present disclosure is not limited thereto. The measurement apparatus 100 may be configured as an independent apparatus for obtaining a tomographic image. For example, the measurement apparatus 100 may be an apparatus including a plurality of the current applying parts 510, a plurality of the magnetic field detecting elements 130, the calculating part 164, and the internal information output part 566.

In this case, a plurality of the magnetic field detecting elements 130 are provided around the measurement target 10, and at least some of the plurality of current applying parts 510 sweep the frequency of the AC current applied to the measurement target 10, for example. Then, the calculating part 164 calculates the impedance of a portion of the measurement target 10 and the frequency characteristic of the impedance corresponding to the frequency of the AC current, based on the detection results of the plurality of magnetic field detecting elements 130. Thus, the internal information output part 566 can generate an image based on the calculated impedance distribution, and an internal state of the measurement target 10 based on the frequency characteristic of the impedance.

In other words, the measurement apparatus 100 of the third configuration example can measure an image of the inside of the measurement target 10 and an internal state, by applying an AC current to the measurement target 10 without applying a magnetic field. The measurement apparatus 100 may further include the mounting part 140 and the moving part 150 described above.

In the measurement apparatus 100 according to the present embodiment described above, an example has been described in which an AC current or the like is applied to a living body serving as the measurement target 10 in order to acquire information about the inside of the living body, but the present disclosure is not limited thereto. The measurement apparatus 100 may be used for searching for living bodies, or may be used for measuring vital activity of a living body, for example. The following describes such a measurement apparatus 100.

<Fourth Configuration Example of the Measurement Apparatus 100>

Figure 12:
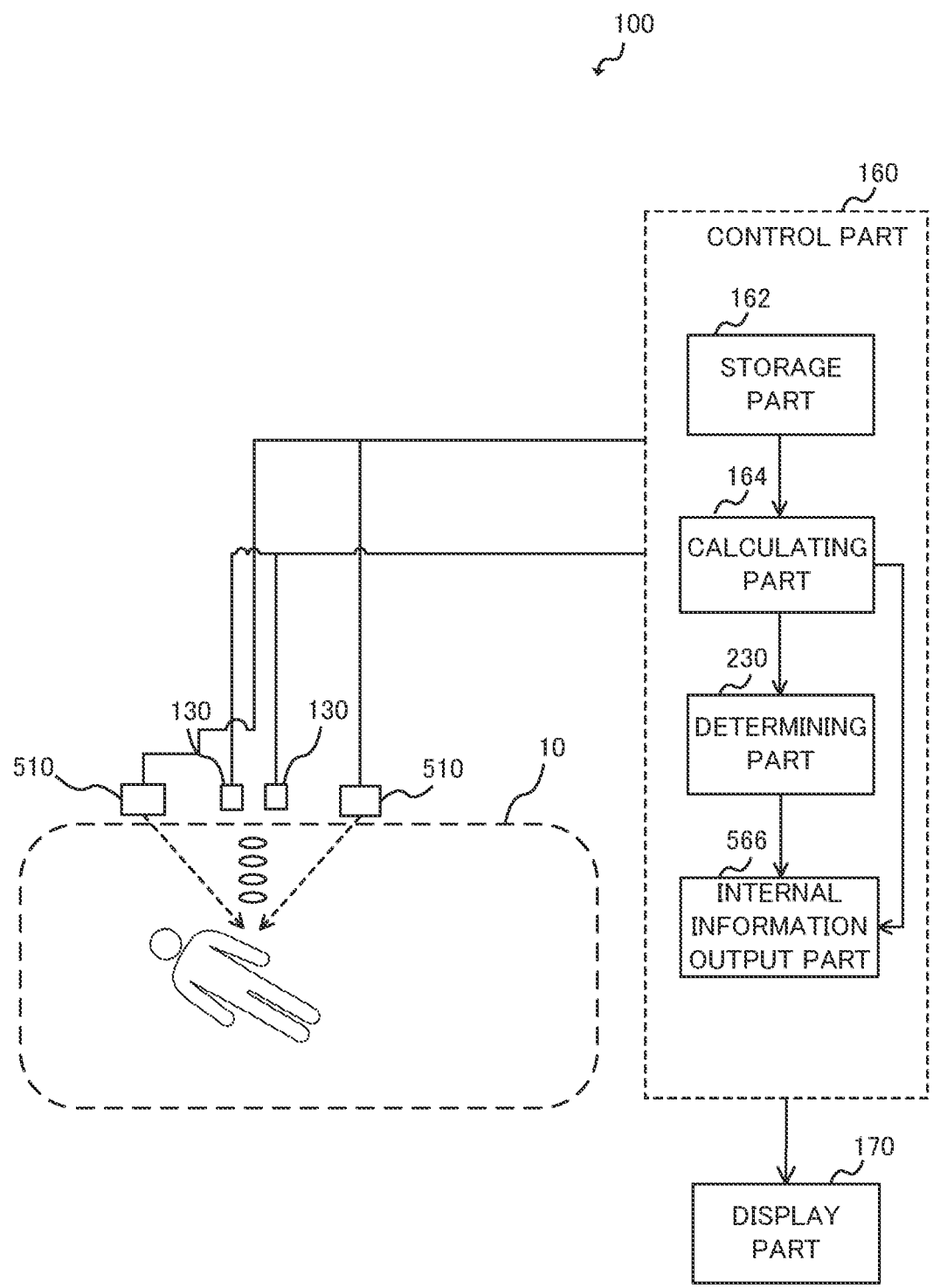
FIG. 12 shows a fourth configuration example of the measurement apparatus 100 according to the present embodiment, together with the measurement target 10.

FIG. 12 shows a fourth configuration example of the measurement apparatus 100 according to the present embodiment, together with the measurement target 10. The measurement apparatus 100 of the fourth configuration example includes a plurality of the current applying parts 510, the magnetic field detecting element 130, the calculating part 164, and the internal information output part 566. As described above, the measurement apparatus 100 is desirably configured as an apparatus independent of the apparatus for outputting the MR image. The measurement apparatus 100 searches for a living body that is trapped in the measurement target 10, with the measurement target 10 being the ground, rubble, a building, or the like.

The plurality of current applying parts 510 apply a plurality of AC currents oriented in a plurality of directions, from a plurality of positions in the measurement target 10 toward portions of the measurement target 10, through the pair of electrodes. The magnetic field detecting element 130 detects the magnitude of the magnetic field generated from the portions of the measurement target 10 according to the plurality of AC currents. A plurality of the magnetic field detecting elements 130 may be provided. Even though the portion of the measurement target 10 to which the AC current is applied is not a living body, if a magnetic field is generated by electromagnetic induction, the magnetic field detecting element 130 detects the magnitude of the generated magnetic field. If a magnetic field hardly occurs in the portion to which the AC current is applied, the detection amount of the magnetic field by the magnetic field detecting element 130 becomes zero.

The calculating part 164 calculates the impedance of the portion of the measurement target 10 based on the detection result of the magnetic field detecting element 130. The internal information output part 566 generates information including internal components of the measurement target 10, based on the calculated impedance. For example, the value of the impedance varies depending on the component of the portion to which the AC current is applied, such as a living body, soil, concrete, stone, or wood. Accordingly, it is possible to determine whether or not a living body exists in the measurement target 10 even in a state where a person is trapped in the ground, under rubble, in a building, or the like due to a natural disaster or the like and where the living body cannot be visually recognized from outside the measurement target 10.

In the measurement apparatus 100 of the fourth configuration example, it is desirable to apply AC current to a plurality of portions of the measurement target 10 to measure whether or not a living body exists in the plurality of portions. In this case, it is desirable that the measurement apparatus 100 measures the impedance distribution of a predetermined region of the measurement target 10 and measures the range of impedance corresponding to a living body. Thus, since the measurement apparatus 100 can generate an image of a predetermined region corresponding to the impedance distribution, the user or the like can determine whether a person exists or some other animal or the like exists inside the measurement target 10, by visually recognizing the size, the schematic shape, and the like of the living body.

Further, the measurement apparatus 100 may measure the impedance inside the measurement target 10 while comparing the impedance of each portion. For example, the current applying part 510 applies a plurality of AC currents to a first portion and a second portion of the measurement target 10. Then, the calculating part 164 calculates a first impedance based on the detection result of the magnetic field generated from the first portion of the measurement target 10 according to the plurality of AC currents, and a second impedance based on the detection result of the magnetic field generated from the second portion of the measurement target 10 according to the plurality of AC currents. The internal information output part 566 generates information including at least one component of the first portion and the second portion by comparing the calculated first impedance and the second impedance.

In this case, the calculating part 164 may calculate the absolute value of the impedance of a part of the measurement target 10, or may calculate the relative value of the impedance, instead of or in addition to the absolute value. Thus, even when the calculating part 164 calculates the relative value of the impedance, if the measurement apparatus 100 measures the second portion after measuring the first portion, for example, it is possible to confirm whether or not the second portion is the same component as the first portion. Further, the user of the measurement apparatus 100 can determine a third portion to be measured next, by referring to the comparison result between the second portion and the first portion.

At least some of the plurality of current applying parts 510 may sweep the frequency of the AC current applied to the measurement target 10. The calculating part 164 calculates a frequency characteristic of a portion of the impedance of the measurement target 10 based on the detection result of the magnetic field detecting element 130. Due to this, the internal information output part 566 can acquire the spectrum distribution of the induction magnetic field generated in a portion of the measurement target 10, so that the information of the components in this portion of the measurement target 10 can be generated more accurately.

Further, the measurement apparatus 100 of the fourth configuration example may measure a change over time of the impedance in a portion of the measurement target 10. In this case, the current applying part 510 continuously applies a plurality of AC currents for a predetermined period to at least a portion of the measurement target 10. The magnetic field detecting element 130 detects a change over time of the magnitude of the magnetic field generated in a portion of the measurement target 10. The calculating part 164 calculates the impedance of a portion of the measurement target 10 a plurality of times in a predetermined period, and outputs the change over time of the impedance.

For example, a person trapped in the ground, under rubble, in a building, or the like, performs vital activity such as breathing as long as the person survives, even in a situation where the person cannot move freely. Therefore, the change over time of the impedance of the measurement target 10 corresponds to a change accompanying such vital activity. For example, when a change in the position of an organ due to breathing, a change in the position of a person due to movement of the person, a change in the position of rubble or the like due to movement of the person, or the like occurs in a portion where AC current is being applied, the impedance changes over time.

The internal information output part 566 generates information including internal components of the measurement target 10 based on such a change over time of the impedance of a portion of the measurement target 10. For example, the internal information output part 566 outputs information that a living body is moving, in response to a change over time of the impedance. The internal information output part 566 may output information indicating that a component corresponding to the impedance has changed over time.

Further, when the AC current is applied to a plurality of portions of the measurement target 10 to measure a change over time of the impedance of the plurality of portions, the internal information output part 566 may convert the change of the impedance of the plurality of portions into an image or the like and output the image. Thus, the user of the measurement apparatus 100 can determine that a person, an animal, or the like is performing vital activity inside the measurement target 10.

The measurement apparatus 100 of the fourth configuration example described above may be formed as an apparatus housed in a single chassis. In this case, the measurement apparatus 100 may further be provided with wheels or the like so as to be movable on the ground, for example. In this case, the measurement apparatus 100 may be formed so as to be self-propelled. In the measurement apparatus 100, at least a portion including the current applying part 510 and the magnetic field detecting element 130 may be formed separately from the apparatus body. As described above, it is desirable that the measurement apparatus 100 of the fourth configuration example is formed so as to be able to perform measurement while moving to a plurality of positions on the ground of a field, on rubble, or the like.

The present disclosure has been described above on the basis of the exemplary embodiments. The technical scope of the present disclosure is not limited to the scope explained in the above embodiments, and it is obvious to those skilled in the art that various changes and modifications within the scope of the disclosure may be made. An aspect to which such changes and modifications are added can be included in the technical scope of the present disclosure is obvious from the description of the claims.

What is claimed is:

1. A measurement apparatus comprising:
    a static magnetic field applying part that applies a static magnetic field having a constant magnitude in a first direction to a measurement target;
    a plurality of current applying parts that apply a plurality of AC currents oriented in a plurality of directions toward a portion of the measurement target, via a pair of electrodes;
    a magnetic field detecting element that detects a magnitude of a magnetic field of an electromagnetic wave generated due to nuclear magnetic resonance in the portion of the measurement target generated in response to (i) the static magnetic field having the constant magnitude in the first direction and (ii) the plurality of AC currents;
a calculating part that calculates impedance of the portion of the measurement target based on a detection result of the magnetic field detecting element; and
an internal information output part that generates information including an internal component of the measurement target, based on the calculated impedance, wherein
the current applying parts apply the plurality of AC currents to a first portion and a second portion of the measurement target;
the calculating part calculates a first impedance based on a detection result of a magnetic field generated from the first portion of the measurement target according to the plurality of AC currents, and a second impedance based on a detection result of a magnetic field generated from the second portion of the measurement target according to the plurality of AC currents; and
the internal information output part generates information including at least one component of the first portion and the second portion, by comparing the calculated first impedance and the calculated second impedance.

2. The measurement apparatus according to claim 1, further comprising:
a mounting part which has a ring shape or a partial ring shape surrounding the measurement target, and on which one or more of the plurality of the current applying parts are mounted; and
a moving part that moves the mounting part in a predetermined direction while maintaining a direction of the AC currents generated by the one or more current applying parts with respect to the measurement target.

3. The measurement apparatus according to claim 2, wherein
a plurality of the magnetic field detecting elements are provided around the measurement target; and
the mounting part has one or more of the magnetic field detecting elements mounted thereon.

4. A measurement apparatus comprising:
a static magnetic field applying part that applies a static magnetic field having a constant magnitude in a first direction to a measurement target;
a plurality of current applying parts that apply a plurality of AC currents oriented in a plurality of directions toward a portion of the measurement target, via a pair of electrodes;
a magnetic field detecting element that detects a magnitude of a magnetic field of an electromagnetic wave generated due to nuclear magnetic resonance in the portion of the measurement target generated in response to (i) the static magnetic field having the constant magnitude in the first direction and (ii) the plurality of AC currents;
a calculating part that calculates impedance of the portion of the measurement target based on a detection result of the magnetic field detecting element; and
an internal information output part that generates information including an internal component of the measurement target, based on the calculated impedance, wherein
the current applying parts apply the plurality of AC currents continuously for a predetermined period in at least the portion of the measurement target;
the calculating part calculates the impedance of the portion of the measurement target a plurality of times in the predetermined period; and
the internal information output part generates the information including the internal component of the measurement target, based on a change over time of the impedance of the portion of the measurement target.

5. The measurement apparatus according to claim 4, further comprising:
a mounting part which has a ring shape or a partial ring shape surrounding the measurement target, and on which one or more of the plurality of the current applying parts are mounted; and
a moving part that moves the mounting part in a predetermined direction while maintaining a direction of the AC currents generated by the one or more current applying parts with respect to the measurement target.

6. The measurement apparatus according to claim 5, wherein
a plurality of the magnetic field detecting elements are provided around the measurement target; and
the mounting part has one or more of the magnetic field detecting elements mounted thereon.

7. A measurement apparatus comprising:
a static magnetic field applying part that applies a static magnetic field having a constant magnitude in a first direction to a measurement target;
a plurality of current applying parts that apply a plurality of AC currents oriented in a plurality of directions toward a portion of the measurement target, via a pair of electrodes;
a magnetic field detecting element that detects a magnitude of a magnetic field of an electromagnetic wave generated due to nuclear magnetic resonance in the portion of the measurement target generated in response to (i) the static magnetic field having the constant magnitude in the first direction and (ii) the plurality of AC currents;
a calculating part that calculates impedance of the portion of the measurement target based on a detection result of the magnetic field detecting element; and
an internal information output part that generates information including an internal component of the measurement target, based on the calculated impedance, wherein
a plurality of the magnetic field detecting elements are provided around the measurement target;
at least some of the plurality of current applying parts sweep a frequency of one or more of the AC currents applied to the measurement target;
the calculating part calculates the impedance of the portion of the measurement target and a frequency characteristic of the impedance corresponding to the frequency of each AC current and the impedance of the portion of the measurement target, based on detection results of the plurality of magnetic field detecting elements; and
the internal information output part generates information including an internal state of the measurement target, based on the calculated frequency characteristic of the impedance.

8. The measurement apparatus according to claim 7, wherein
the internal information output part further generates an image of the inside of the measurement target, based on the calculated impedance; and the measurement apparatus further comprises a determining part that determines a location in the measurement target at which a state is to be observed by applying the AC currents with the current applying parts, based on the image of the inside of the measurement target generated by the internal information output part.

9. The measurement apparatus according to claim 7, further comprising:
a mounting part which has a ring shape or a partial ring shape surrounding the measurement target, and on which one or more of the plurality of the current applying parts are mounted; and
a moving part that moves the mounting part in a predetermined direction while maintaining a direction of the AC currents generated by the one or more current applying parts with respect to the measurement target.

10. The measurement apparatus according to claim 9, wherein
a plurality of the magnetic field detecting elements are provided around the measurement target; and
the mounting part has one or more of the magnetic field detecting elements mounted thereon.

11. A measurement apparatus comprising:
a static magnetic field applying part that applies a static magnetic field having a constant magnitude in a first direction to a measurement target;
a plurality of current applying parts that apply a plurality of AC currents oriented in a plurality of directions toward a portion of the measurement target, via a pair of electrodes;
a magnetic field detecting element that detects a magnitude of a magnetic field of an electromagnetic wave generated due to nuclear magnetic resonance in the portion of the measurement target generated in response to (i) the static magnetic field having the constant magnitude in the first direction and (ii) the plurality of AC currents;
a calculating part that calculates impedance of the portion of the measurement target based on a detection result of the magnetic field detecting element; and
an internal information output part that generates information including an internal component of the measurement target, based on the calculated impedance, further comprising:
a deflection magnetic field applying part that applies a deflection magnetic field having a predetermined frequency and oriented in a second direction, which is different from the first direction, toward the portion of the measurement target, via a coil;
a relaxation detecting element that detects a relaxation phenomenon of an electromagnetic wave based on the deflection magnetic field generated by the deflection magnetic field applying part, in the portion of the measurement target; and
an MR image generating part that generates and outputs a magnetic resonance image, which is a tomographic image of the inside of the measurement target, based on a detection result of the relaxation detecting element.

12. The measurement apparatus according to claim 11, further comprising:
a determining part that determines a location to be measured in the measurement target by applying the AC currents with the current applying parts, based on the magnetic resonance image generated by the MR image generating part.

13. The measurement apparatus according to claim 12, wherein
the internal information output part further generates an image of the inside of the measurement target, based on the calculated impedance; and
the determining part determines the location in the measurement target at which the magnetic resonance image is to be measured, based on the image of the inside of the measurement target generated by the internal information output part.

14. A measurement apparatus comprising:
a static magnetic field applying part that applies a static magnetic field having a constant magnitude in a first direction to a measurement target;
a plurality of current applying parts that apply a plurality of AC currents oriented in a plurality of directions toward a portion of the measurement target, via a pair of electrodes;
a magnetic field detecting element that detects a magnitude of a magnetic field of an electromagnetic wave generated due to nuclear magnetic resonance in the portion of the measurement target generated in response to (i) the static magnetic field having the constant magnitude in the first direction and (ii) the plurality of AC currents;
a calculating part that calculates impedance of the portion of the measurement target based on a detection result of the magnetic field detecting element; and
an internal information output part that generates information including an internal component of the measurement target, based on the calculated impedance, wherein
the measurement apparatus is provided in an MR image measurement apparatus that includes:
the static magnetic field applying part;
a deflection magnetic field applying part that applies a deflection magnetic field having a predetermined frequency and oriented in a second direction, which is different from the first direction, toward the portion of the measurement target, via a coil;
a relaxation detecting element that detects an electromagnetic wave generated by the application of the deflection magnetic field and a relaxation phenomenon of the generated electromagnetic wave, in the portion of the measurement target; and
an MR image generating part that generates and outputs a magnetic resonance image, which is a tomographic image of the inside of the measurement target, based on a detection result of the relaxation detecting element;
at least some of the plurality of current applying parts sweep a frequency of one or more of the AC currents applied to the measurement target;
the calculating part calculates a frequency characteristic of impedance corresponding to the frequency of each AC current; and
the internal information output part generates information indicating an internal state of the measurement target, based on the calculated frequency characteristic of the impedance.

15. The measurement apparatus according to claim 14, further comprising:
a determining part that determines a location in the measurement target at which the AC currents are to be applied by the current applying parts, based on the magnetic resonance image generated by the MR image generating part.

16. The measurement apparatus according to claim 15, wherein the internal information output part further generates an internal image of the measurement target, based on the calculated impedance; and the determining part determines the location in the measurement target at which the magnetic resonance image is to be measured, based on the internal image of the measurement target generated by the internal information output part.

17. A measurement method comprising:

applying a static magnetic field having a constant magnitude in a first direction to a measurement target;

applying a plurality of AC currents oriented in a plurality of directions toward a portion of the measurement target, via a pair of electrodes;

detecting a magnitude of a magnetic field of an electromagnetic wave generated due to nuclear magnetic resonance in the portion of the measurement target generated in response to (i) the static magnetic field having the constant magnitude in the first direction and (ii) the plurality of AC currents;

calculating impedance of the portion of the measurement target based on the detected magnitude of the magnetic field; and generating and outputting information indicating an internal component of the measurement target, based on the calculated impedance, wherein the applying the plurality of AC currents includes sweeping a frequency of one or more of the AC currents among the plurality of AC currents applied to the measurement target;

the detecting the magnitude of the magnetic field generated from the portion of the measurement target includes detecting the magnitude of the magnetic field generated from the portion of the measurement target in accordance with the plurality of AC currents, at each of a plurality of positions around the measurement target;

the calculating the impedance of the portion of the measurement target includes calculating a frequency characteristic of the impedance corresponding to a frequency of each AC current; and the generating information indicating the internal component of the measurement target includes generating information including an internal state of the measurement target based on the calculated frequency characteristic of the impedance.

18. The measurement method according to claim 17, comprising:

applying the plurality of AC currents oriented in the plurality of directions, from around the measurement target toward the portion of the measurement target, via the pair of electrodes;

detecting the magnitude of the magnetic field generated from the portion of the measurement target in response to the AC currents, at a plurality of positions around the measurement target;

calculating the impedance of the portion of the measurement target based on the detected magnitude of the magnetic field;

generating an image of the inside of the measurement target, based on the calculated impedance;

determining a location to be measured in the measurement target by applying the AC currents, based on the image of the inside the measurement target; and after the determining the location to be measured by applying the AC currents, repeating the measurement method to generate information indicating a state of the determined location to be measured.

19. The measurement method according to claim 17, comprising:

applying the plurality of AC currents oriented in the plurality of directions, from around the measurement target toward the portion of the measurement target via the pair of electrodes;

detecting the magnitude of the magnetic field generated from the portion of the measurement target in response to the AC currents, at a plurality of positions around the measurement target;

calculating the impedance of the portion of the measurement target based on the detected magnitude of the magnetic field;

generating an image of the inside of the measurement target based on the calculated impedance;

determining a location in the measurement target where a magnetic resonance image is to be generated, based on the image of the inside of the measurement target;

applying a static magnetic field having a constant magnitude in the first direction to the measurement target;

applying a deflection magnetic field having a predetermined frequency and oriented in a second direction, which is different from the first direction, toward the determined location in the measurement target where the magnetic resonance image is to be generated, via a coil;

detecting an electromagnetic wave generated due to the application of the deflection magnetic field oriented in the second direction and a relaxation phenomenon of the generated electromagnetic wave, in the portion to be measured;

generating and outputting the magnetic resonance image, which is a tomographic image of the inside of the measurement target, based on the detected electromagnetic wave;

determining a location to be measured in the measurement target by applying the AC currents, based on the magnetic resonance image; and after the determining the location to be measured by applying the AC currents, repeating the measurement method to generate information indicating a state of the determined location to be measured.

* * * * *